United States Patent
Meade et al.

(10) Patent No.: US 9,585,975 B2
(45) Date of Patent: Mar. 7, 2017

(54) MRI CONTRAST AGENTS

(71) Applicant: NORTHWESTERN UNIVERSITY, Evanston, IL (US)

(72) Inventors: Thomas J. Meade, Wilmette, IL (US); Renee C. Strauch, Charlotte, NC (US); Luke F. Vistain, Chicago, IL (US)

(73) Assignee: Northwestern University, Evanston, IL (US)

( * ) Notice: Subject to any disclaimer, the term of this patent is extended or adjusted under 35 U.S.C. 154(b) by 792 days.

(21) Appl. No.: 13/853,324

(22) Filed: Mar. 29, 2013

(65) Prior Publication Data
US 2013/0302258 A1    Nov. 14, 2013

Related U.S. Application Data

(60) Provisional application No. 61/639,549, filed on Apr. 27, 2012.

(51) Int. Cl.
*A61K 49/10* (2006.01)
*A61K 49/12* (2006.01)
*A61K 49/14* (2006.01)

(52) U.S. Cl.
CPC .......... *A61K 49/108* (2013.01); *A61K 49/126* (2013.01); *A61K 49/14* (2013.01)

(58) Field of Classification Search
CPC ..... A61K 49/108; A61K 49/14; A61K 49/126
See application file for complete search history.

(56) References Cited

U.S. PATENT DOCUMENTS

| | | | | |
|---|---|---|---|---|
| 2011/0201024 A1* | 8/2011 | Wood | ........................ | C12N 9/14 435/7.6 |
| 2011/0268663 A1* | 11/2011 | Bates | .................... | A61K 49/085 424/9.363 |

OTHER PUBLICATIONS

Strauch et al., J. Am. Chem. Soc., 2011, 133, p. 16346-16349.*
Mastarone et al., J. Am. Chem. Soc., 2011, 133 (14), p. 5329-5337.*
Aime, S. et al., "Ternary Gd(III)L-HSA adducts: evidence for the replacement of inner-sphere water molecules by coordinating groups of the protein. Implications for the design of contrast agents for MRI", JBIC (2000), 5: 488-497.
Caravan, P. et al., "Gadolinium(III) Chelates as MRI Contrast Agents: Structure, Dynamics, and Applications.", Chem. Rev. 1999, 99, 2293-2352.
Caravan, P. et al., "Influence of molecular parameters and increasing magnetic field strength on relaxivity of gadolinium- and manganese-based T1 contrast agents", Contrast Media and Mol. Imaging 2009, 4, 89-100.
Caravan, P. et al., "The Interaction of MS-325 with Human Serum Albumin and Its Effect on Proton Relaxation Rates", J. Am. Chem. Soc. 2002, Vol. 124, No. 12, 3152-3162.
Ferreira, M. et al., "Gd(DO3A-N-alpha-aminopropionate): a versatile and easily available synthon with optimized water exchange for the synthesis of high relaxivity, targeted MRI contrast agents", Chem. Commun. 2009, 6475-6477.
Hata, T. et al, "Rapid single-tube method for small-scale affinity purification of polyclonal antibodies using HaloTag™ Technology", J. Biochem. Biophys. Methods 70 (2007), pp. 679-682.
Los, G. and K. Wood, "The HaloTag™: A novel technology for cell imaging and protein analysis", Methods in Molecular Biol. vol. 356 (2009), pp. 195-208.
McCabe, P. H. et al., "Conformational study of bridgehead lactams. Preparation and X-ray structural analysis of 1-azabicyclo[3.3.1]nonane-2,6-dione" J. Chem. Soc., Perkin Trans. 2 1989, 1459-1462.
Zech, S. G. et al., "Probing the Water Coordination of Protein-Targeted MRI Contrast Agents by Pulsed ENDOR Spectroscopy" ChemPhysChem 2005, 6, 2570-2577.

* cited by examiner

*Primary Examiner* — Michael G Hartley
*Assistant Examiner* — Leah Schlientz
(74) *Attorney, Agent, or Firm* — Casimir Jones, S.C.

(57) ABSTRACT

The present invention relates to MRI based imaging. In particular, the present invention provides MRI contrast agents targeted to a HaloTag protein with tunable relaxation properties thereby providing optimal relaxivity for low field strength imaging and the other optimal relaxivity for high field strength imaging. Moreover, the MRI contrast agents are used to detect gene expression (of a gene of interest) in real time in vivo, to detect changes in gene expression (of a gene of interest) over time in, for example, an individual organism, to detect gene expression changes (of a gene of interest) in response to therapeutics, in cell labeling for MR imaging, in clinical diagnostics, and in theranostics.

5 Claims, 13 Drawing Sheets

LV27

LV19

US 9,585,975 B2

MRI CONTRAST AGENTS

STATEMENT REGARDING FEDERALLY SPONSORED RESEARCH OR DEVELOPMENT

This invention was made with government support under 5R01EB005866-06 awarded by the National Institutes of Health. The government has certain rights in the invention.

FIELD OF THE INVENTION

The present invention relates to MRI based imaging. In particular, the present invention provides MRI contrast agents targeted to a HaloTag protein with tunable relaxation properties thereby providing optimal relaxivity for low field strength imaging and the other optimal relaxivity for high field strength imaging. Moreover, the MRI contrast agents are used to detect gene expression (of a gene of interest) in real time in vivo, to detect changes in gene expression (of a gene of interest) over time in, for example, an individual organism, to detect gene expression changes (of a gene of interest) in response to therapeutics, in cell labeling for MR imaging, in clinical diagnostics, and in theranostics.

BACKGROUND OF THE INVENTION

Magnetic resonance imaging (MRI) is a diagnostic tool in both research and clinical applications due to its capacity to render images of high spatial and temporal resolution without the need for ionizing radiation (see, e.g., Frullano, L.; Meade, T. J. J. Biol. Inorg. Chem. 2007, 12, 939; herein incorporated by reference in its entirety). Contrast agents, such as chelated Gd(III), can be utilized in clinical MR imaging to improve sensitivity and resolution as well as allow more rapid scanning times (see, e.g., Caravan, P.; Ellison, J. J.; McMurry, T. J.; Lauffer, R. B. Chem. Rev. 1999, 99, 2293; herein incorporated by reference in its entirety). While valuable information can be attained using generic contrast agents, their effectiveness is limited due to their nonspecificity, rapid clearance, and low relaxivity (see, e.g., Caravan, P.; Ellison, J. J.; McMurry, T. J.; Lauffer, R. B. Chem. Rev. 1999, 99, 2293; herein incorporated by reference in its entirety).

Improved contrast agents for use in clinical MRI imaging are needed.

SUMMARY

Magnetic Resonance Imaging (MRI) is an indispensable tool for clinical diagnosis. MRI non-invasively produces a three dimensional image by placing a target in a magnetic field and exciting the nuclear spins of water protons using radio frequency pulses. The radio frequency pulse shifts the proton spins out of alignment with the magnetic field. As the spins relax back to alignment, energy is released which can be measured and used to produce an image. The signal intensity in a given volume is proportional to the concentration of water protons and the rates that they relax. There are two major relaxation rates. Decreasing $T_1$ relaxation produces a positive contrast, brightening images. Decreasing $T_2$ relaxation has the opposite effect.

MRI has a combination of spatial resolution and tissue penetration that is unique among imaging modalities. MRI can image deep tissue whereas optical imaging suffers from light scattering that limits deep tissue resolution. Unlike X-Ray, positron emission tomography (PET), or CT, patients can be repeatedly imaged using MRI due to the lack of ionizing radiation. Other detection methods such as PET have a much higher sensitivity, but they are unable to achieve the level of spatial resolution of MRI is capable of. MRI sensitivity is limited compared to other imaging modalities, but this can be overcome in part through the use of contrast agents.

The Gd(III) ion is a commonly used paramagnetic contrast agent. Several Gd(III)-chelates are routinely used to enhance clinical MR images. Gd(III) has a property referred to as relaxivity, which improves contrast by reducing the $T_1$ relaxation rate of nearby protons from water. Gd(III) creates an area of increased brightness in an MRI image because the intensity of the MRI signal is proportional to the relaxation rate of water. The increased signal intensity can be used to improve resolution, reduce acquisition times, or mark a location of interest. Modifying the properties of the chelate enables the creation of targeted agents or "smart" agents that respond to their environment. The present invention provides several Gd(III)-chelate agents that can identify locations of interest (e.g., tissues expressing estrogen receptor or areas of elevated β-galactosidase activity).

HaloTag is an engineered protein that covalently binds to a variety of haloalkane ligand. This binding occurs rapidly under physiological conditions and is essentially irreversible. HaloTag and its ligands make a unique binding pair in vivo because haloalkanes are generally absent from biological systems. Due to the versatility of haloalkanes in organic synthesis, many useful molecules can be easily bound to HaloTag. These include fluorescent dyes, quantum dots, biotin, and PET agents.

Experiments conducted during the course of developing embodiments for the present invention describes the synthesis and characterization of several Gd(III) chelates capable of binding to HaloTag. It was determined that a two-carbon linker in 2CHTGd is optimized for a field strength of 60 MHz, which is close to MR instruments most commonly used in the clinic. At clinical field strengths the ideal rotation rate of the Gd(III) chelate is as slow as possible. The slower rotation caused by binding to a protein causes a significant increase in relaxivity for the optimized agent. Binding creates more than a fivefold increase in relaxivity specific to the site of HaloTag. Second-generation contrast agents such as multinuclear and agents designed for high field strength. These have multiple Gd(III)-chelates attached to a single haloalkane ligand. The increases in relaxivity scale roughly linearly with the number of Gd(III) ions, thus multiple Gd(III) ions result in a large increase in relaxivity per HaloTag protein.

Accordingly, the present invention relates to MRI based imaging. In particular, the present invention provides MRI contrast agents targeted to a HaloTag protein with tunable relaxation properties thereby providing optimal relaxivity for low field strength imaging and the other optimal relaxivity for high field strength imaging. Moreover, the MRI contrast agents are used to detect gene expression (of a gene of interest) in real time in vivo, to detect changes in gene expression (of a gene of interest) over time in, for example, an individual organism, to detect gene expression changes (of a gene of interest) in response to therapeutics, in cell labeling for MR imaging, in clinical diagnostics, and in theranostics.

In certain embodiments, the present invention provides compositions comprising an MRI contrast agent selected from the group consisting of LV19, LV27, 1CHTGd, 2CHTGd, 3CHTGd, and 4CHTGd. In some embodiments, the MRI contrast agent is configured to attach with a HaloTag protein. In some embodiments, the MRI contrast agents have tunable relaxation properties thereby providing optimal relaxivity for low field strength imaging and the other optimal relaxivity for high field strength MR imaging.

In certain embodiments, the present invention provides methods of imaging, comprising expressing a HaloTag/gene of interest construct in a cell, administering a MRI contrast agent configured to attach with said Halo Tag/gene of interest, and imaging said attached MRI contrast agent with said Halo Tag/gene of interest. In some embodiments, the MRI contrast agent is selected from the group consisting of LV19, LV27, 1CHTGd, 2CHTGd, 3CHTGd, and 4CHTGd. In some embodiments, the imaging relates to detecting gene expression (of a gene of interest) in real time in vivo, detecting changes in gene expression (of a gene of interest) over time in, for example, an individual organism, detecting gene expression changes (of a gene of interest) in response to therapeutics, and detecting cell labeling for MR imaging.

DETAILED DESCRIPTION OF THE INVENTION

Figure 1:
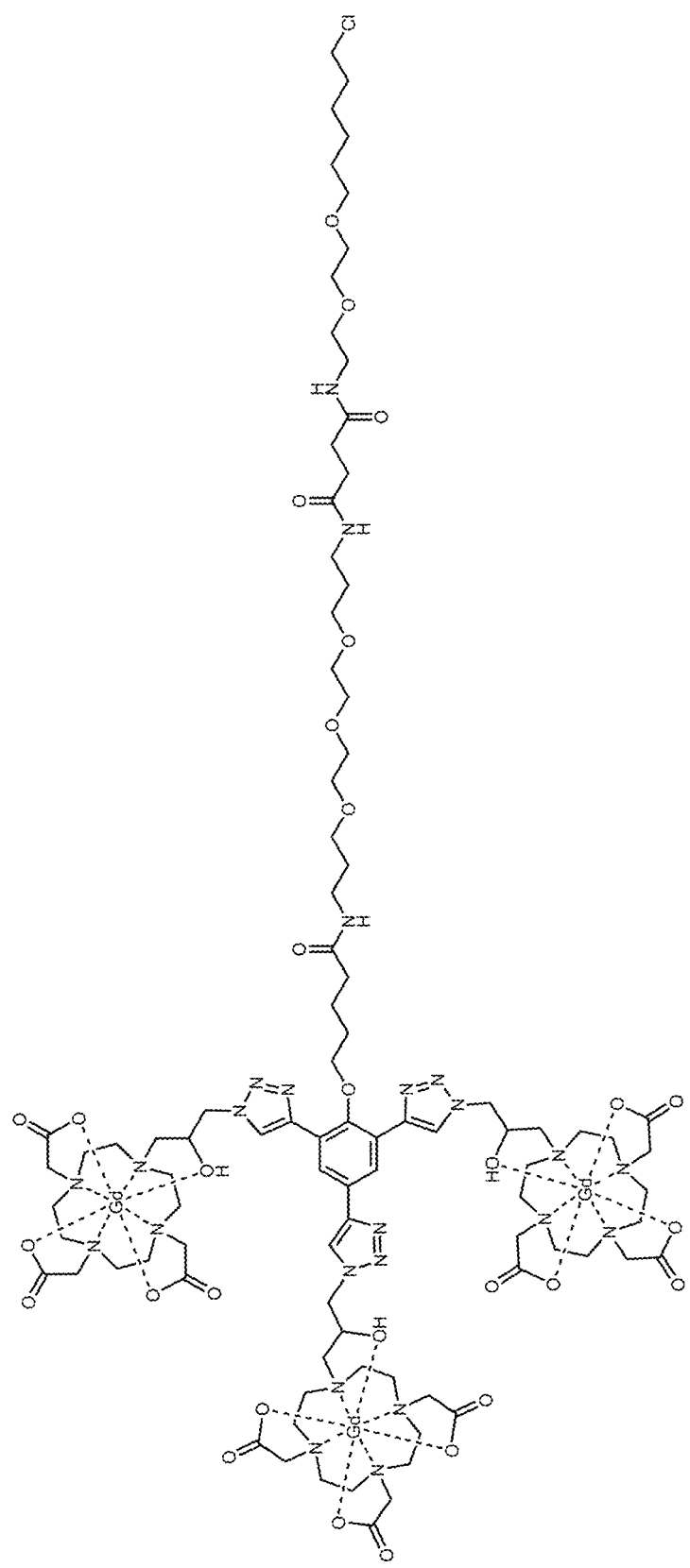
FIG. 1 shows LV27.

The ability to optically label proteins through genetic modification has becomes a central facet of biological research. Despite its obvious usefulness, methods that include proteins such as green fluorescence protein, yellow fluorescent protein, luciferase etc. all have significant drawbacks. Any experiment which requires a change in the wavelength of the reporter protein will necessitate a change in the organism's genetic construction. Also, reporter genes that rely on visible light are limited to transparent organisms or thin tissue slices. Recent developments in protein engineering have yielded a protein (HaloTag) that has the potential to solve the problem of single wavelength reporting (see, e.g., G. Los, K. Wood, The HaloTag: A novel technology for cell imaging and protein analysis, Meth. In mol. biol. 356 (2009), pp. 195-208; herein incorporated by reference in its entirety). The present invention incorporates MRI contrast agents instead of optically active agents into the Halo Tag system thereby rendering it possible to, for example, image organisms that would not normally be compatible with the commonly used reporter genes.

HaloTag is a genetically engineered protein which is based on a bacterial hydrolase (haloalkane dehalogenase) (see, e.g., G. Los, K. Wood, The HaloTag: A novel technology for cell imaging and protein analysis, Meth. In mol. biol. 356 (2009), pp. 195-208; herein incorporated by reference in its entirety). Normally the output that can be measured from a reporter gene is unique to the protein produced by the gene. HaloTag overcomes this limitation by conferring the ability to covalently bind a specific organic ligand rather than having a unique output. This ligand can then be attached to other molecules to produce the desired output. Recent work with HaloTag has taken advantage of this ability by attaching biotin for use as an affinity handle, quantum dots for imaging, and resin for antibody purification and cell immobilization (see, e.g., G. Los, K. Wood, The HaloTag: A novel technology for cell imaging and protein analysis, Meth. In mol. biol. 356 (2009), pp. 195-208; T. Hata, M Nakayama, Rapid single-tube method for small-scale affinity purification of polyclonal antibodies using Halotag Technology, Biochem. biophys. methods 70 (2007), pp. 679-682; M. So, H. Yao, J Rao, Halotag protein-mediated specific labeling of live cells with quantum dots, Biochem. biophys. res. commun. 374 (2008) pp. 419-423; each herein incorporated by reference in its entirety).

The present invention utilizes the Halo Tag technology through attaching an MRI contrast agent to the haloalkane ligand thereby generating MRI signal output. MRI adds several advantages that would be difficult to obtain using other imaging methods. Because it doesn't use visible light it can be used to study tissues and opaque cells. Furthermore, MRI imaging can be performed on multicellular organisms over long periods of time, which is difficult with light based systems.

MRI contrast agents improve the sensitivity of images by increasing the relaxation rate of solvent water molecules. The capacity for a contrast agent to do this is referred to as its relaxivity ($r_1$ or $r_2$) which is defined as the change in the water relaxation rate per unit concentration. The most commonly used contrast agents are gadolinium based, which have a high $r_1$ relaxivity. High $r_1$ relaxivity is preferable over $r_2$ relaxivity because $r_1$ produces a positive contrast, which brightens the image, while $r_2$ produces negative contrast. There are three primary molecular parameters that describe a contrast agent's interaction with water and affect relaxivity. The first parameter is the number of water molecules that can be bound to the gadolinium at one time (q), the second parameter is the rate at which these water molecules exchange ($\tau_m$), and the third is a measure of the rate that the complex tumbles in solution ($\tau_r$). Of particular interest is $\tau_r$, as increasing the rate of rotation increases the relaxivity at low external field strength (see, e.g., P. Caravan et al., Influence of molecular parameters and increasing magnetic field strength on relaxivity of gadolinium- and manganese-based T1 contrast agents, Cont. Media and mol. imag. 28 (2009), pp. 89-100; herein incorporated by reference in its entirety). This property can be used to target the MRI contrast agent. Ideally an agent would have low enough relaxivity to only give a weak signal while free in solution, but upon binding to its target, rotation would slow and the agent would have relaxivity high enough to serve as an effective contrast agent (see, e.g., P. Caravan et al., Influence of molecular parameters and increasing magnetic field strength on relaxivity of gadolinium- and manganese-based T1 contrast agents, Cont. Media and mol. imag. 28 (2009), pp. 89-100; herein incorporated by reference in its entirety). Additionally, protein bound contrast agent will remain in the specimen longer, which allows more imaging time and improves the signal to noise ratio as unbound contrast agent is cleared. While this property is very useful at field strengths between 0.5 and 1.5 T, it poses problems at higher field strengths. Above 1.5 T the rule that slower tumbling results in higher relaxivity breaks down and there becomes a specific rotation rate that serves as the optimal rate for maximizing $r_1$ relaxivity (see, e.g., P. Caravan et al., Influence of molecular parameters and increasing magnetic field strength on relaxivity of gadolinium- and manganese-based T1 contrast agents, Cont. Media and mol. imag. 28 (2009), pp. 89-100; herein incorporated by reference in its entirety).

The present invention addresses the optimization of $\tau_r$ values for MRI contrast agents. Indeed, experiments conducted during the course of developing embodiments for the present invention involved the designing of HaloTag compatible MRI contrast agents by optimizing the $\tau_r$ values of HaloTag targeted contrast agents. Such experiments demonstrated that while contrast agents free in solution have relaxivities that are invariant under different field strengths, this is not true for the slow rotating molecules produced by a fusion with HaloTag. In the past medical imaging has generally been below 2 T but it is becoming increasingly common to image at higher fields and most research imaging is done well above this limit due to the improved resolution given by higher field strengths (see, e.g., P. Caravan et al., Influence of molecular parameters and increasing magnetic field strength on relaxivity of gadolinium- and manganese-based T1 contrast agents, Cont. Media and mol. imag. 28 (2009), pp. 89-100; herein incorporated by reference in its entirety). Accordingly, the present invention provides contrast agents that can rotate at the optimal rate upon binding to targets to be useful in MRI used in research and medicine in the near future. In some embodiments, adjusting the length of the linker region between the HaloTag protein and the contrast agent optimizes $\tau_r$, as the length and nature of the linker region determines how much of the rotation of the protein is coupled to the rotation of the contrast agent.

Experiments conducted during the course of developing embodiments for the present invention synthesized, characterized, and purified improved MRI contrast agents (e.g., LV19 and LV27). This was accomplished through standard solution synthesis techniques, silica chromatography separation, high pressure liquid chromatography (HPLC) for purification, and matrix-assisted laser desorption/ionization (MALDI) for characterization of the target compounds. The relaxivity of each of the improved MRI contrast agents (e.g., LV19 and LV27) both free in solution and bound to the HaloTag protein was determined.

Accordingly, the present invention is not limited to particular improved MRI contrast agents. In some embodiments, the present invention provides LV27 (see, e.g., FIG. 1):

Figure 1

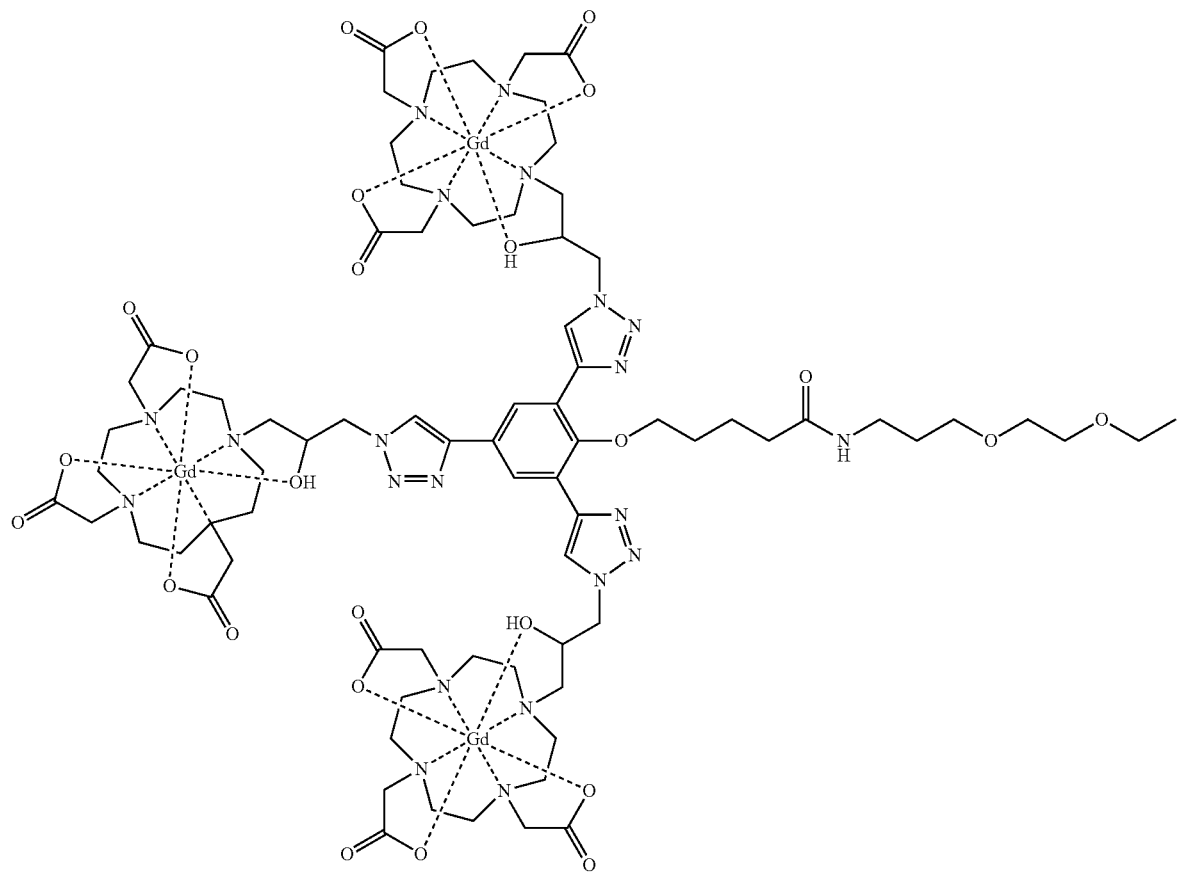

LV27

-continued

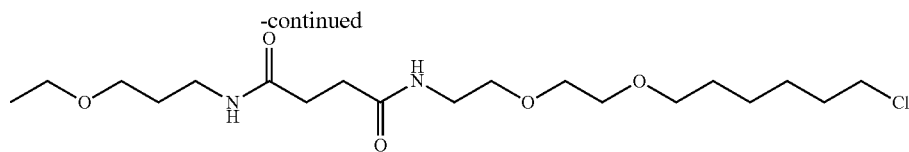

Figure 2:
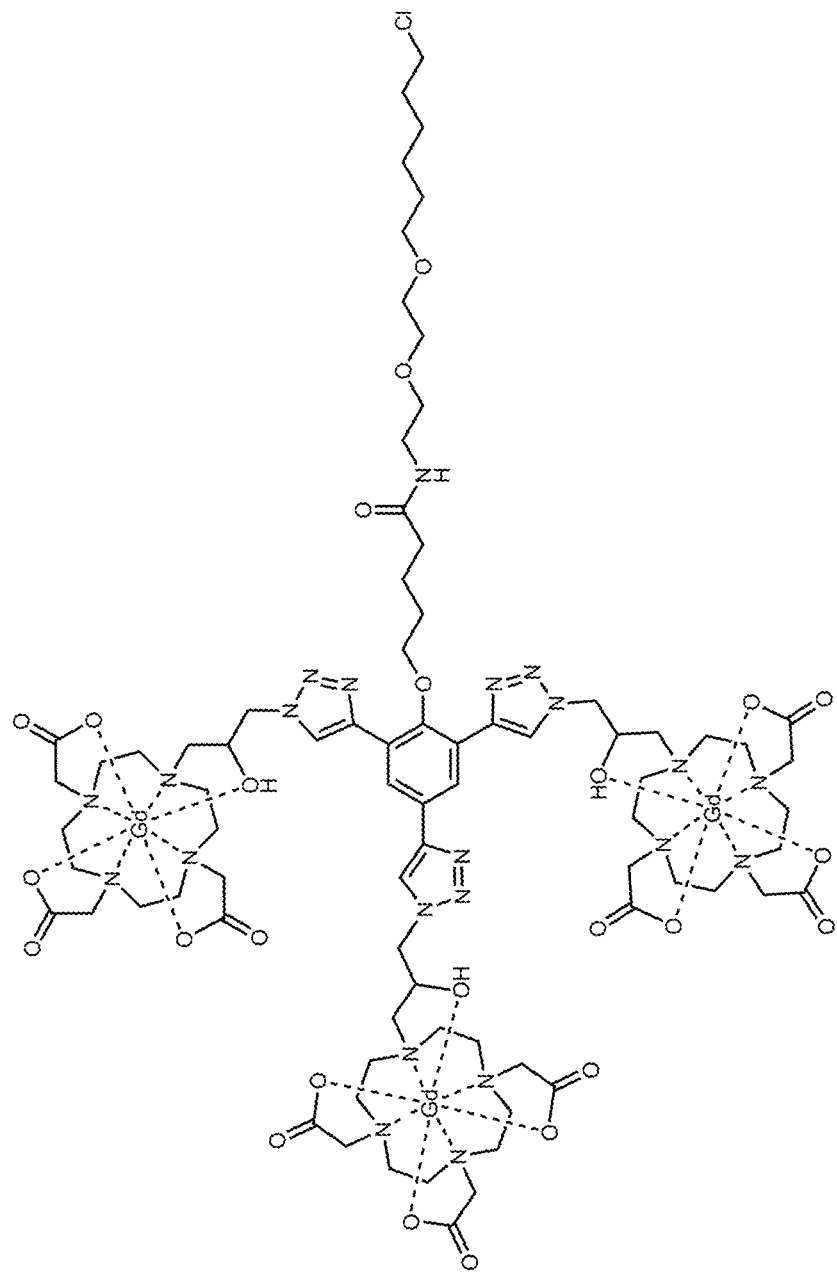
FIG. 2 shows LV19.

In some embodiments, the present invention provides LV19 (see, e.g., FIG. 2):

Figure 2

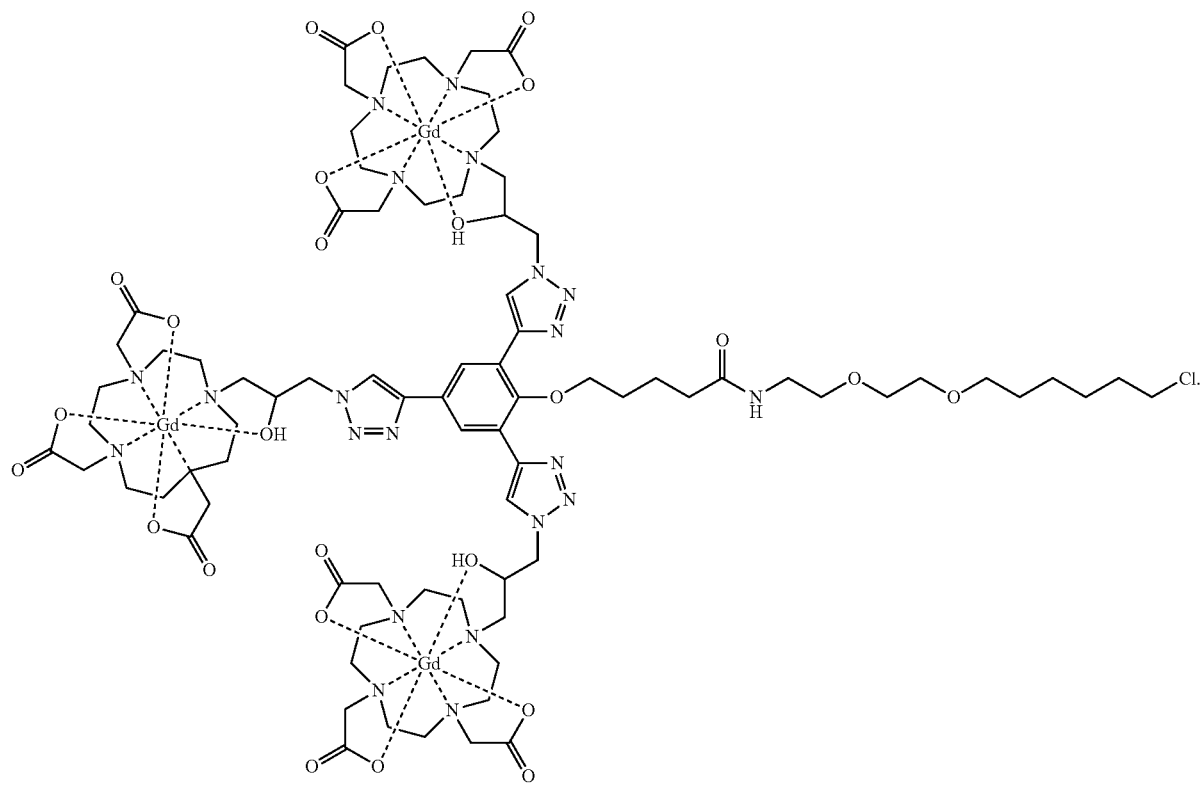

LV19

Figure 12:
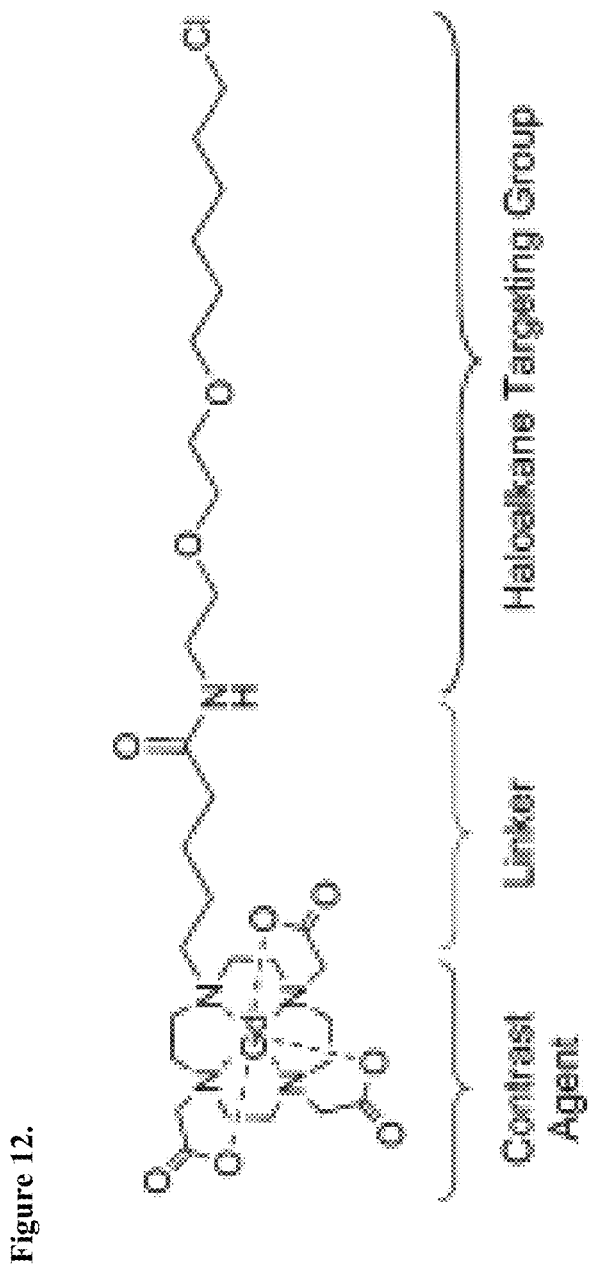
FIG. 12 shows HaloTag-targeted contrast agents. A macrocyclic Gd(III) chelator is connected to a haloalkane group via a flexible linker to generate a HaloTag-targeted contrast agent. Four complexes, with linkers of 1 to 4 carbons (shown).

In some embodiments, the present invention provides the MRI contrast agents shown in FIG. 12 and synthesis schemes 1 and 2.

The improved MRI contrast agents (LV19 and LV27) provide significant advantages over existing contrast agents. For example, LV19 and LV27 offer better spatial resolution than PET, bioluminescence, CT, and/or ultrasound.

The present invention is not limited to particular uses for the improved MRI contrast agents of the present invention (LV19 and LV27).

The present invention is not limited to particular linking moeities for facilitating securing of the improved MRI contrast agents with a Halo Tag entity.

The present invention is not limited to particular uses of the improved MRI contrast agents (LV19 and LV27). Current reporter gene systems suffer from severe limitation in in vivo experiments. Reporter genes that offer high spatial resolution generally require sacrificing of the subject, which results in a loss of temporal resolution. Reporter genes that offer temporal resolution often lose spatial resolution. In some embodiments, the present invention permits direction of Gd(III) based MRI contrast agents specifically to locations that have HaloTag expression. This allows such systems to take advantage of MRI's excellent spatial and temporal resolution.

The present invention is not limited to the fusion of a particular gene to the Halo Tag entity. Indeed, any gene of interest can be used (e.g., CD28 or TLR4 gene).

In some embodiments, the improved MRI contrast agents are used, for example, to detect gene expression (of a gene of interest) in real time in vivo.

In some embodiments, the improved MRI contrast agents are used, for example, to detect changes in gene expression (of a gene of interest) over time in, for example, an individual organism.

In some embodiments, the improved MRI contrast agents are used, for example, detect gene expression changes (of a gene of interest) in response to therapeutics.

In some embodiments, the improved MRI contrast agents are used, for example, in cell labeling for MR imaging.

In some embodiments, the improved MRI contrast agents are used, for example, in clinical diagnostics.

In some embodiments, the improved MRI contrast agents are used, for example, in theranostics.

The present invention is not limited to a particular manner of molecular cloning of Halo Tag. For example, experiments conducted during the course of developing embodiments for the present invention followed the following procedure. In order for HaloTag to be accessible to injected contrast agent, it must be expressed extracellularly. To prevent diffusion of HaloTag (and dilution of contrast enhancement) it must remain bound to the plasma membrane. Following literature precedent, this has been accomplished by creating a fusion protein in which HaloTag is flanked by a signal peptide directing it to the plasma membrane on one side and a transmembrane domain on the other. Two different fusion proteins were designed to hedge the risk of either construct failing. The signal peptide and transmembrane domain were taken from the CD28 or TLR4 gene. For each construct the signal peptide gene matches the transmembrane gene. The plasmid encoding this construct was built using staggered overlap extension polymerase chain reaction (PCR) to join the signal peptide, HaloTag, and transmembrane segments. The resulting PCR product was cloned upstream of a CMV promoter in PC DNA 3.1 plasmid and verified using Sanger sequencing and restriction digest analysis.

The present invention is not limited to particular fluorescence based verification of Halo Tag function. Several tests are underway to validate the function of the HaloTag construct. Expression of the construct will be observed by using any of a variety of commercially available fluorescent dyes modified to include a haloalkane ligand. Effective cell staining will indicate that HaloTag is functional because it is able to bind to haloalkane ligands. Overexpressing transmembrane proteins can result in failure to properly traffic them to the plasma membrane. Trafficking can be monitored with confocal microscopy by first dyeing the cells with cell impermeable Alexa 488 followed by cell permeable coumarin.

Two tests will be performed to determine the protein half-life and surface expression. Following literature precedent, HaloTag half-life can be determined by dyeing cells and performing SDS-PAGE at various times after dyeing. The dye remains covalently bound to HaloTag after denaturation. After staining the cells flow cytometry will be used to quantify the number of fluorescent dye molecules displayed on the surface of each cell. This procedure will allow determination of the number of HaloTag proteins expressed and available for labeling on the cell surface.

Once a functioning HaloTag construct has been characterized, it will be tested for its ability to bind to targeted MRI contrast agents and enhance contrast. Cells expressing the HaloTag construct will be labeled with 2CHTGd. MR images of cell pellets will be taken to ensure sufficient contrast is produced. Relaxivity measurements at 1.41 T will be taken to determine the relaxivity improvement conferred by the contrast agent. Cells with and without the HaloTag construct will be compared after incubation with 2CHTGd. Inductively coupled plasma mass spectrometry (ICP-MS) and flow cytometry will be used to calculate the number of Gd(III) ions associated with each cell and cell viability.

In some embodiments, it may be necessary to amplify the signal produced by the reporter gene. The ultimate goal of signal amplification in this system is to increase the number of Gd(III) ions bound to the cell when the promoter is active. The MRI contrast agents of the present invention provide several features that allow for such amplification. At the promoter level, additional operator segments can be included to induce more expression of the HaloTag gene. At the protein level, the HaloTag gene can be modified such that several HaloTag units are fused together separated by glycine/serine linkers. At the chemical level, the current generation of multinuclear contrast agents does not represent the limit of the number of Gd(III) ions that can be conjugated to a single haloalkane ligand.

EXPERIMENTAL

The following examples are provided in order to demonstrate and further illustrate certain preferred embodiments and aspects of the present invention and are not to be construed as limiting the scope thereof.

Example 1

Figure 3:
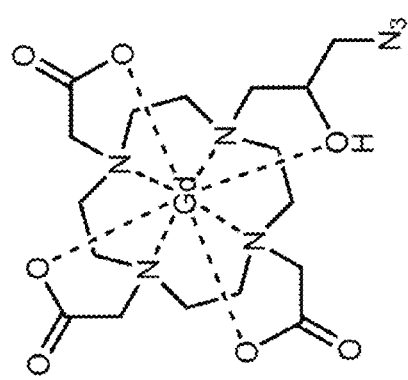
FIG. 3 shows ProN3.

Both target compounds were produced using common synthesis techniques. A first goal was to produce the compounds indicated in FIGS. 1 and 2 which will be referred to as LV27 and LV19 respectively. Intermediates of these compounds were purified through the use of silica gel chromatography and characterized through electron spray ionization mass spectroscopy (ESI-MS) and nuclear magnetic resonance (NMR). ProN3, the compound displayed in FIG. 3, was then attached to these intermediate compounds using click chemistry to yield the final product displayed in FIGS. 1 and 2. The final products were then purified by HPLC and characterized by MALDI.

Figure 4:
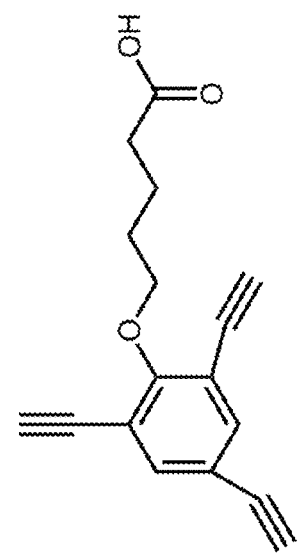
FIG. 4 shows C3-Acid.
Figure 6:
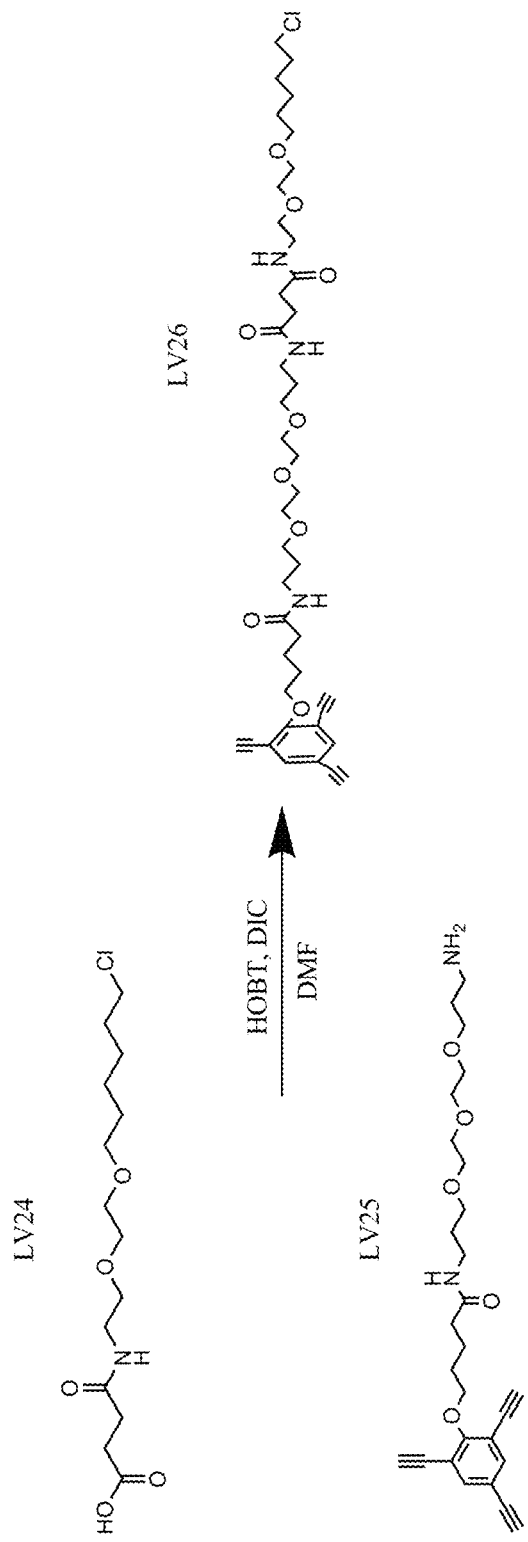
FIG. 6 shows a synthesis scheme for LV26.
Figure 7:
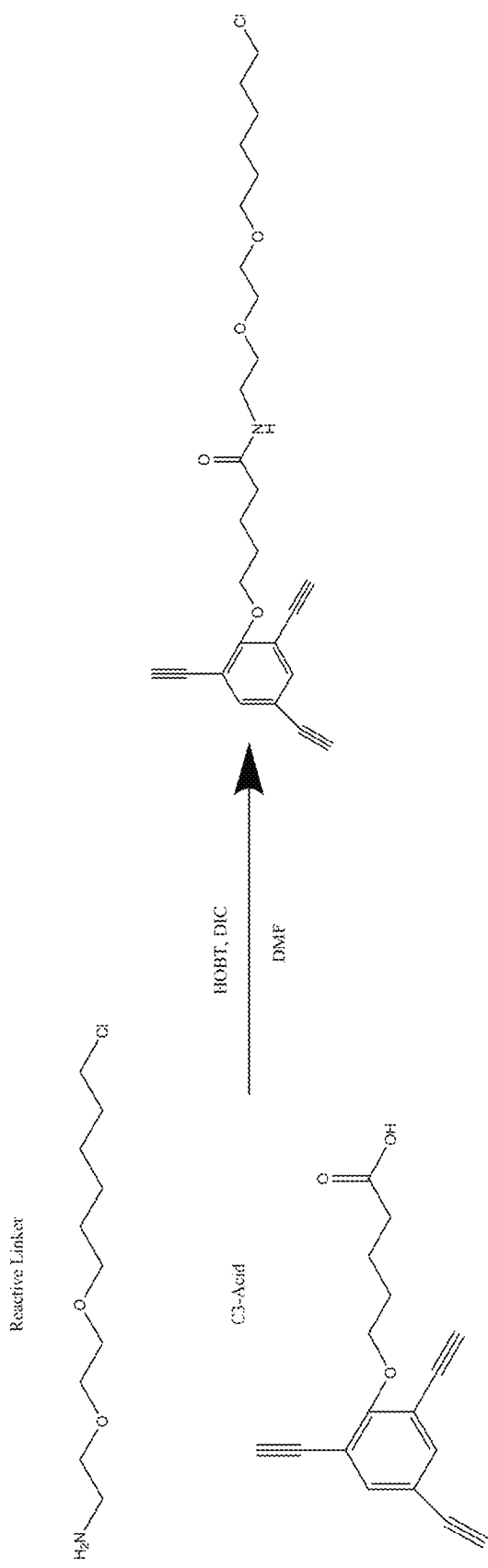
FIG. 7 shows a synthesis scheme wherein LV19 was produced from a peptide coupling of C3-Acid to the reactive linker.
Figure 8:
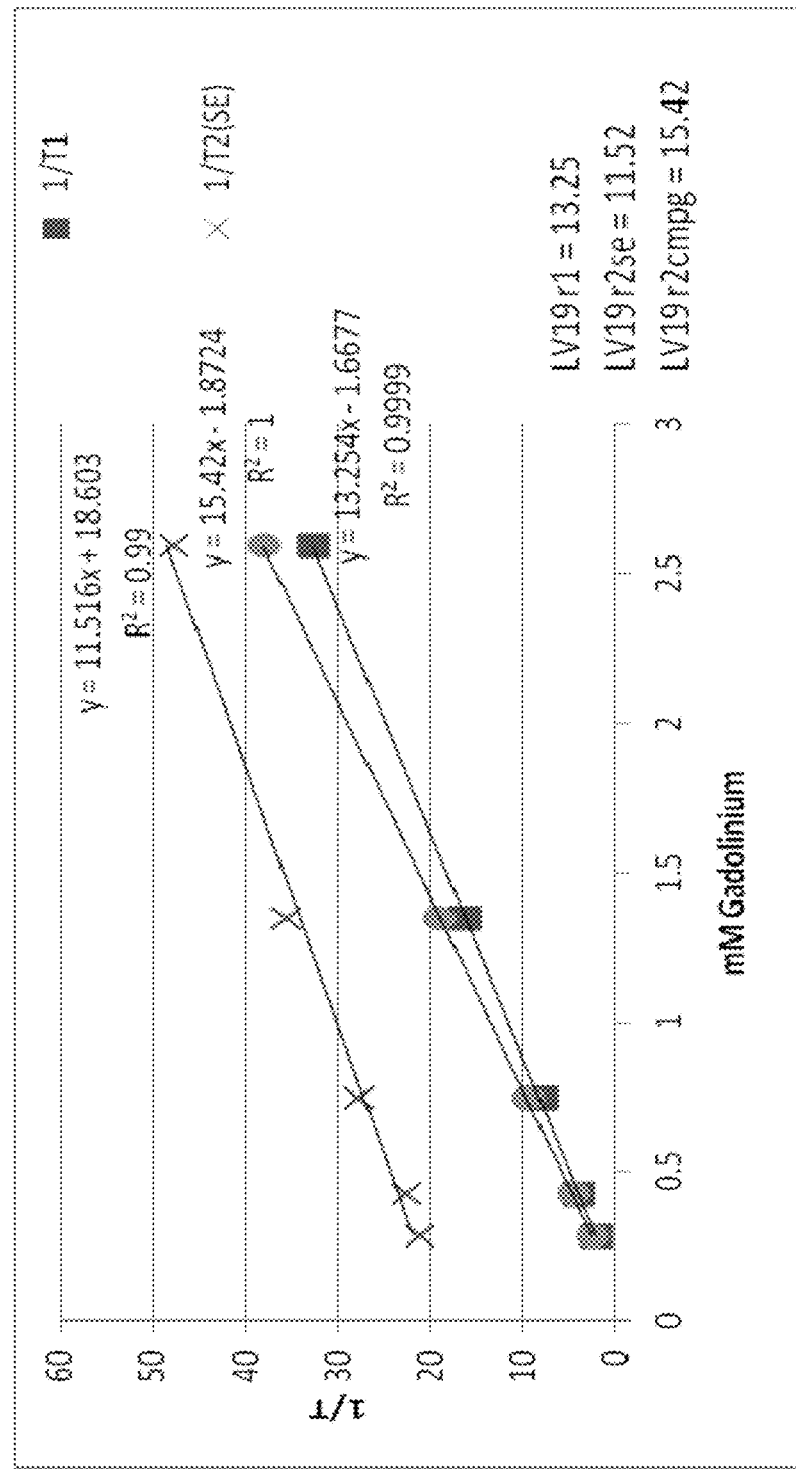
FIGS. 8, 9, 10 and 11 show s relaxivity data for LV19.
Figure 9:
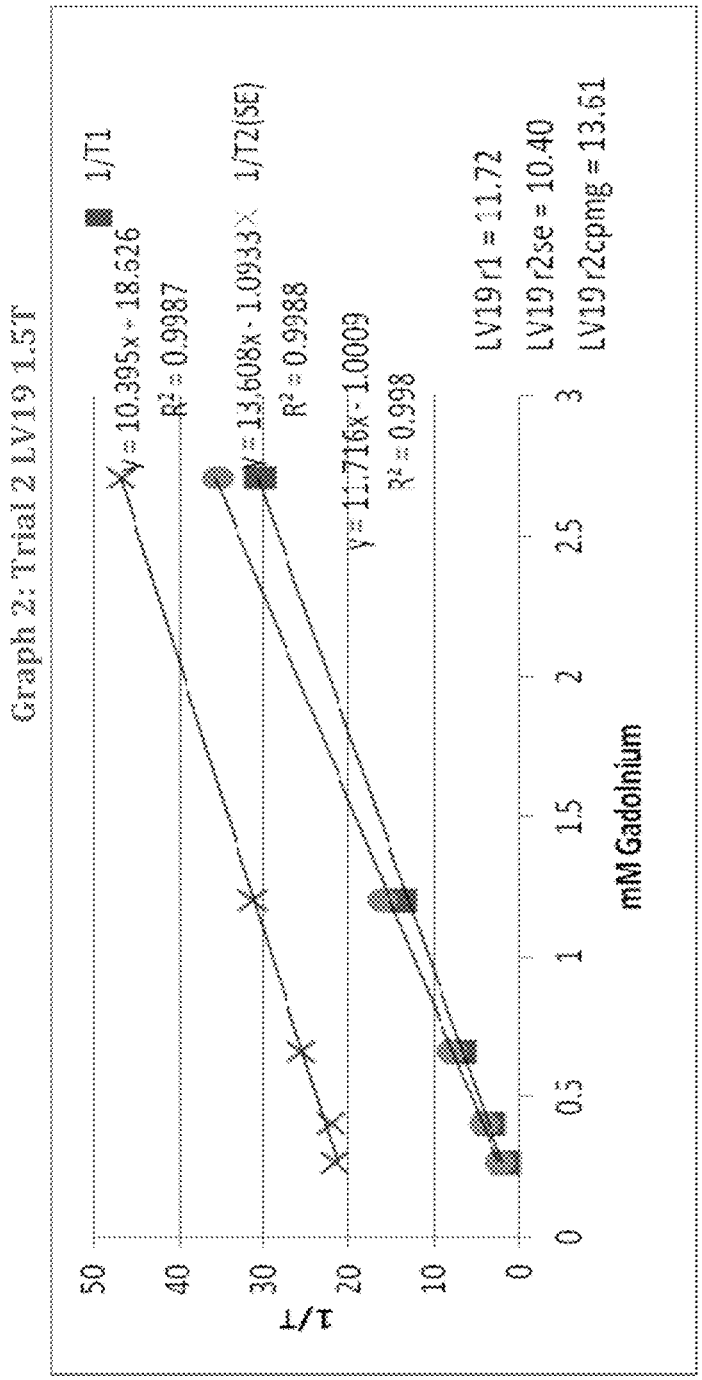
Figure 10:
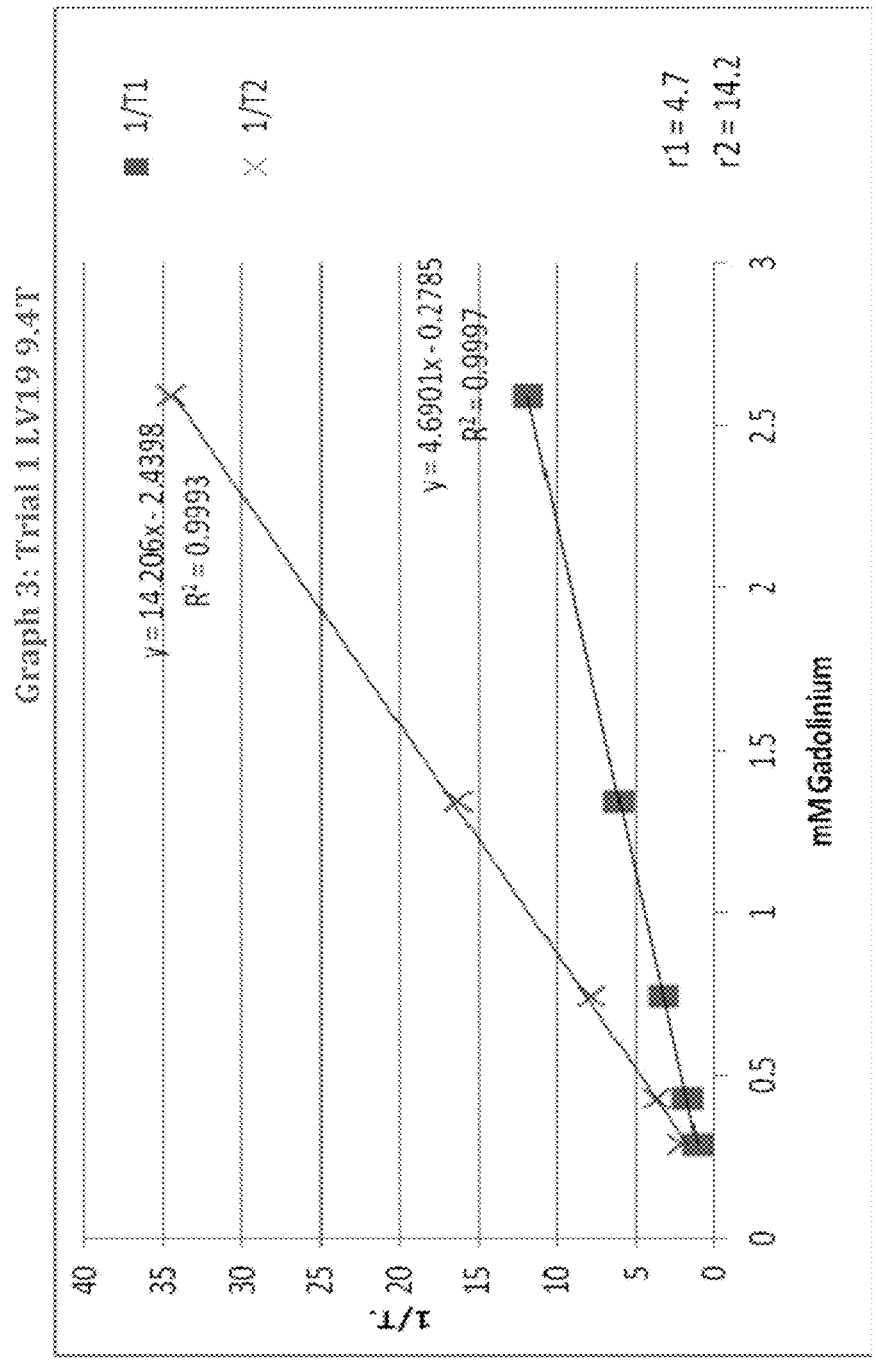
Figure 11:
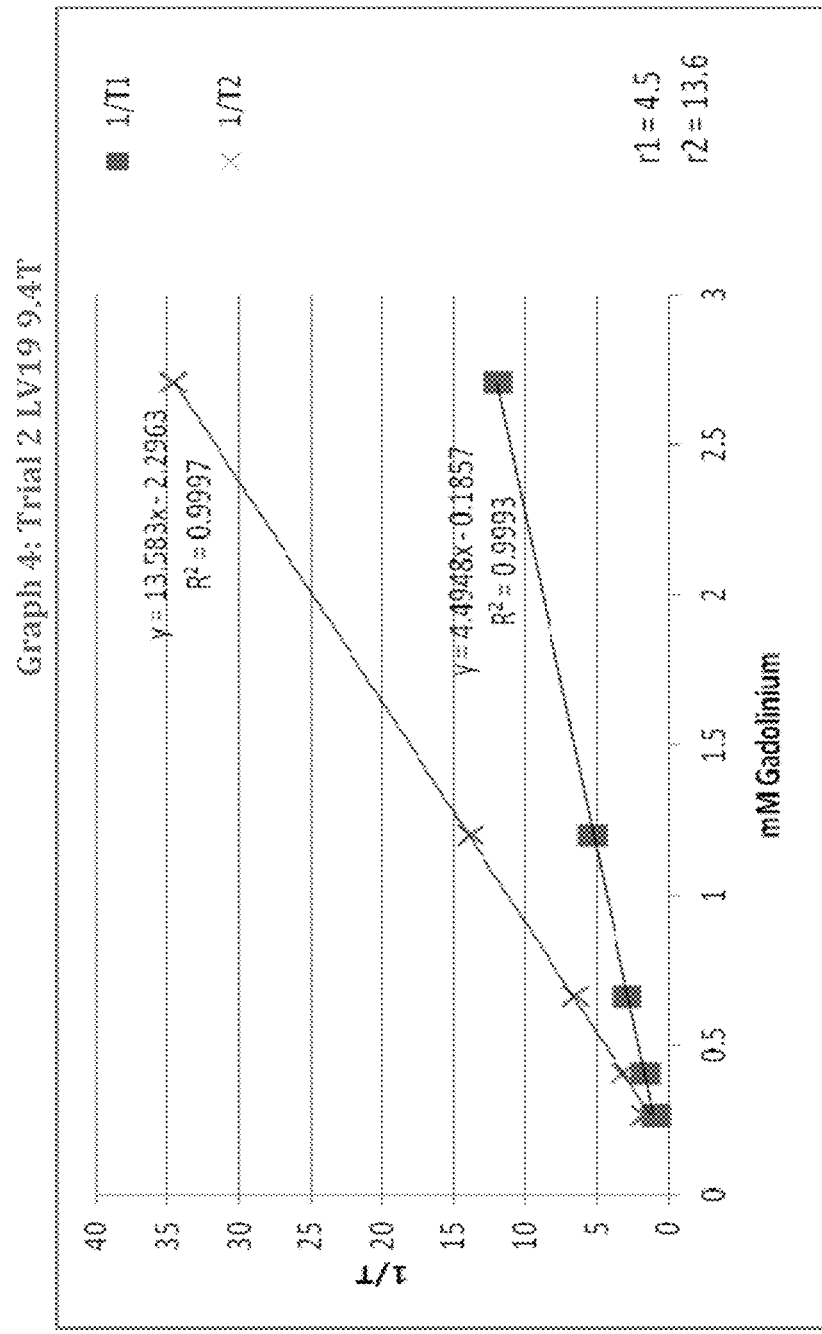

The synthesis of the target compounds was relatively straightforward. Previous research produced C3-Acid (FIG. 4) and ProN3 (FIG. 3), and the remaining steps involved synthesizing the linker region between the C3-Acid and the HaloTag ligand. LV19 was produced from a peptide coupling of C3-Acid to the reactive linker (FIG. 7) followed addition of 3 ProN3 molecules by click chemistry. The desired product of the first reaction was purified by column chromatography and characterized by NMR. These methods are unsuitable for characterizing the final product which was instead purified by HPLC and characterized by MALDI. The synthesis of LV27 is more complicated, and was accomplished through a series of peptide couplings, one to produce a long linker attached to C3-Acid, and another to attach a linker to the HaloTag ligand. These two products were then peptide coupled together to form LV26, the precursor to LV27 (FIG. 6). As before, each of these steps was characterized through NMR and eventually attached to ProN3 through click chemistry. This final product was purified through HPLC and characterized by MALDI.

In order to measure relaxivity of bound LV19 and LV27, a supply of HaloTag protein was made. A previously created strain of E. Coli that stably expresses HaloTag with a histidine tag and TEV protease cleavage site that will allow for the removal of the His tag after purification was used. This strain was grown, the cells lysed, and the HaloTag protein was purified on a Ni affinity column. After purification they were be treated with TEV protease. This mixture was then allowed to flow over a Ni affinity column again, causing the His tags and TEV protease to bind to the column and allow HaloTag to flow out, yielding pure protein.

Relaxation times were measured for LV19 and LV27 free in solution at both high and low field strength. Low field strength measurements were performed on a standard 1.5 T relaxometer. High field strength measurements were taken at IMSERC at 9.4 T. In both instances relaxation times for T1 and T2 were measured for a range of concentrations in order to determine relaxivity. Exact concentrations were determined by inductively coupled mass spectrometry (ICP-MS).

Five-fold excess of LV19 and LV27 samples were then incubated with HaloTag protein overnight and dialyzed overnight. The labeled protein solution was then concentrated. Relaxation and ICP-MS measurements were taken of these solutions.

The synthesis of LV19 required only 2 steps. C3-Acid (376 μmol) was combined with hydroxybenzotriazole (HOBT 451 μmol) and diisopropylcarbodiimide (DIC 451 μmol) in dry dimethylformamide (DMF) under dry conditions. This was allowed to react for 30 minutes. Reactive linker (451 μmol) was then dissolved in dry DMF. This was added to the reaction mixture and allowed to react overnight. The reaction mixture was washed several times with water and dried with brine. The product was purified using column chromatography. The product was eluted from the column through addition of one column volume of 1:2 ethyl acetate:hexanes, followed by one column volume of a 1:1 solution, followed by one column volumes of a 1:2 solution etc. until all spots displayed on TLC were eluted. This method produced a 50% yield and verified by NMR.

The second step required the use of click chemistry to attach ProN3. The product of the previous reaction (190 μmol) was dissolved in 2 ml t-butanol and combined with ProN3 (672 μmol) dissolved in 2 ml water. Copper I (19 μmol) and Tris-[(1-benzyl-1H-1,2,3-triazol-4-n yl)methyl] amine (TBTA 19 μmol) was added and the reaction allowed to mix overnight. It was determined by MALDI that the reaction was only partially complete, with a mixture of products with 0, 1, 2, or 3 ProN3 groups attached. Each group was subjected to additional click reactions as necessary with a 1.1 ProN3/product molar ratio for each missing ProN3 group. In this instance, cupric sulphate and sodium ascorbate was used instead of Copper I and TBTA. This product was then purified by HPLC and verified to be the complete LV19 molecule by MALDI.

Figure 5:
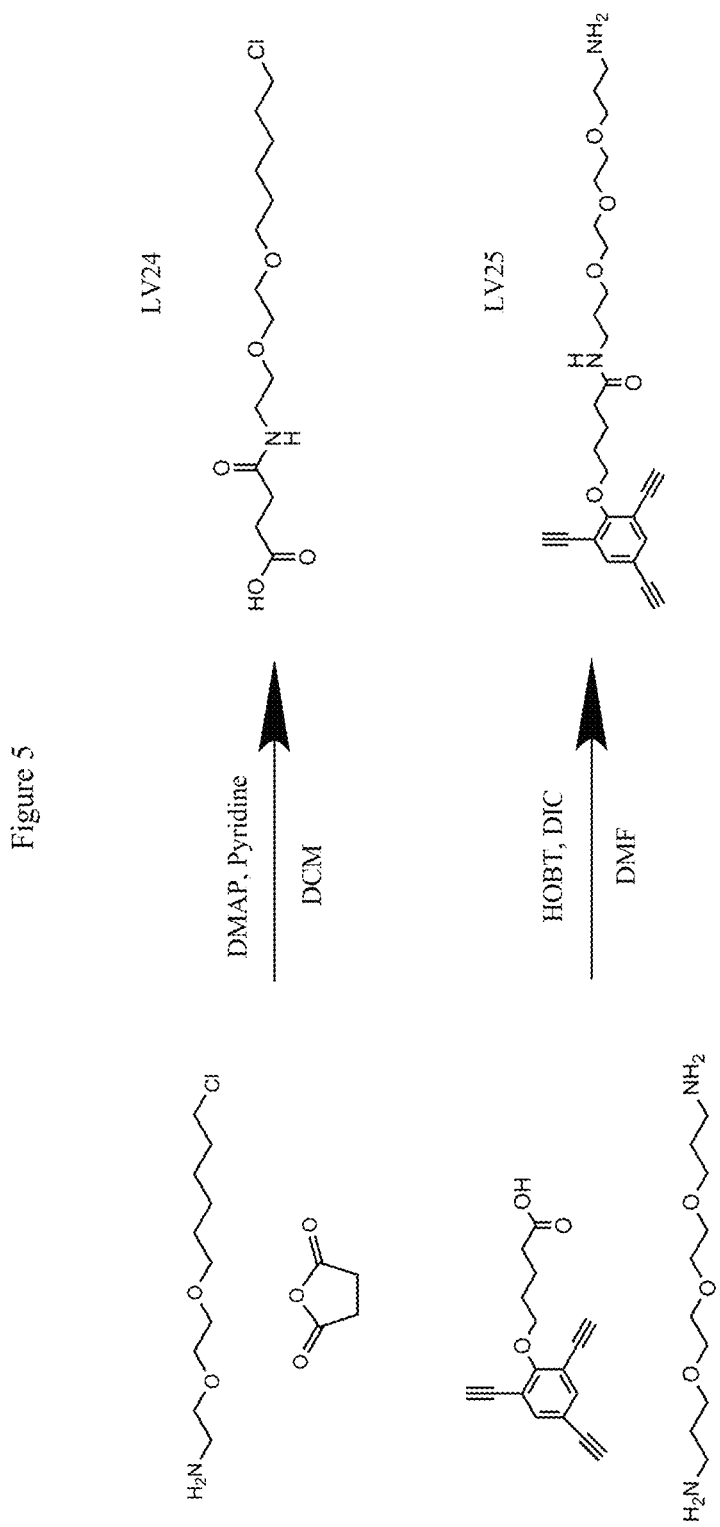
FIG. 5 shows a synthesis scheme for LV24 and LV25.

The first step in the production of LV27 is the creation of LV24 (FIG. 5). Under dry conditions the reactive linker (0.45 mmol) and 4-dimethylaminopyridine (DMAP 0.045 mmol) were dissolved in dry dichloromethane (DCM). Succinic acid anhydride (0.9 mmol) and pyridine (4.5 mmol) was added and allowed to mix overnight. The reaction mixture was then washed several times with water and dried with brine. The product was confirmed by ESI-MS and NMR.

The second step in the production of LV27 is the creation of LV25 (FIG. 5). C3-Acid (1.1 mmol) was dissolved in dry DMF under dry conditions and mixed with DIC (1.4 mmol) and HOBT (1.4 mmol). After 30 minutes the amine (3.3 mmol) was dissolved in dry DMF and added to the reaction mixture. The reaction was allowed to occur overnight and the resulting mixture washed several times with water and dried with brine. The product was characterized by ESI-MS and NMR.

The third step in the production of LV27 is the creation of LV26 (FIG. 6). LV24 (0.207 mmol) was dissolved in dry DMF under dry conditions and mixed with DIC (1.4 mmol) and HOBT (0.248 mmol). After 30 minutes LV25 (0.19 mmol) was dissolved in dry DMF and added to the reaction mixture. The reaction was allowed to occur overnight and the resulting mixture washed several times with water and finally brine. The final product was purified by column chromatography.

The final step of the reaction is to perform click chemistry on LV26 with ProN3. ProN3 (0.54 mmol) was dissolved in 2 ml water and LV26 (0.13 mmol) was dissolved in 1.5 ml t-butanol. Cupric sulphate (0.052 mmol copper) was combined with sodium ascorbate (0.156 mmol) in 0.5 ml water. All 3 mixtures were combined and allowed to mix overnight. The final product was purified by HPLC and characterized by MALDI.

The relaxivity of LV19 was then determined at two field strengths. Relaxation rates were first taken at 1.5 T ($T_1$, $T_2$ spin echo, and $T_2$-CPMG were measured) over a range of concentrations. This experiment was done in duplicate and then repeated at 9.4 T (in this instance, $T_1$ and $T_2$ were determined). The samples used to produce this data were then subjected to ICP-MS analysis to determine the exact gadolinium concentration. These data were then used to determine relaxivity for unbound LV19. The results of all 4 trials are displayed in FIGS. 8, 9, 10, and 11.

Example II

This example describes the synthesis of a series of four MR probes containing a Gd(III) chelate and a haloalkane substrate connected by linkers of varying lengths (FIG. 12). These derivatives were designed to systematically shorten the distance between the Gd(III) chelate and the surface of the protein in order to exploit a receptor-induced magnetization enhancement (RIME) (see, e.g., Aime, S.; J. Biol. Inorg. Chem. 2000, 5, 488; Caravan, P.; J. Am. Chem. Soc. 2002, 124, 3152; each herein incorporated by reference in its entirety) effect and to optimize binding to the protein. It was hypothesized that restricting the local motion of the Gd(III) chelate near the flexible linker would result in longer rotational correlation times and, therefore, increased relaxivity. The complexes are referred to by the number of carbons in the linker excluding the carbonyl carbon, the HaloTag targeting group, and the Gd(III) ion (1CHTGd, 2CHTGd, 3CHTGd, and 4CHTGd).

The synthesis of the amine-terminated HaloTag targeting moiety is described in Supplemental Scheme 1. 1-Amino-2-ethoxyethanol was carbobenzyloxy (CBZ) protected using benzyl chloroformate and TEA to produce S1. 1-Bromo-6-chlorohexane was coupled in 40% KOH in water using tert-butyl ammonium hydroxide as a phase transfer catalyst to produce S2. The protecting group was removed via hydrogenation with a palladium on carbon catalyst to produce the amine-terminated haloalkane species (S3) for peptide coupling to the Gd(III) chelate-linker molecule.

Scheme 1. Two Synthetic Routes Coupling Gd(III) Chelators and Variable Length Linkers Towards the Formation of a HaloTag-Targeted Contrast Agent Series

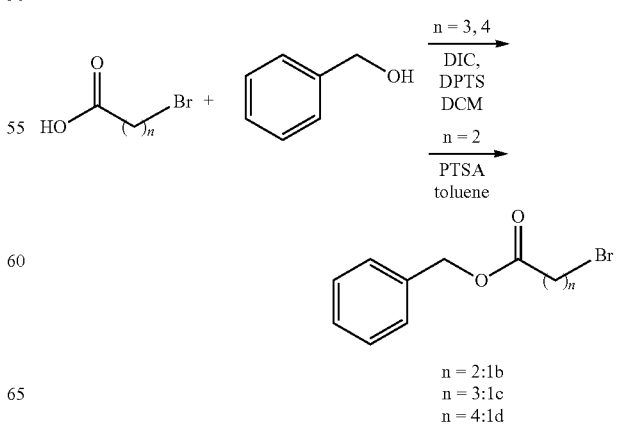

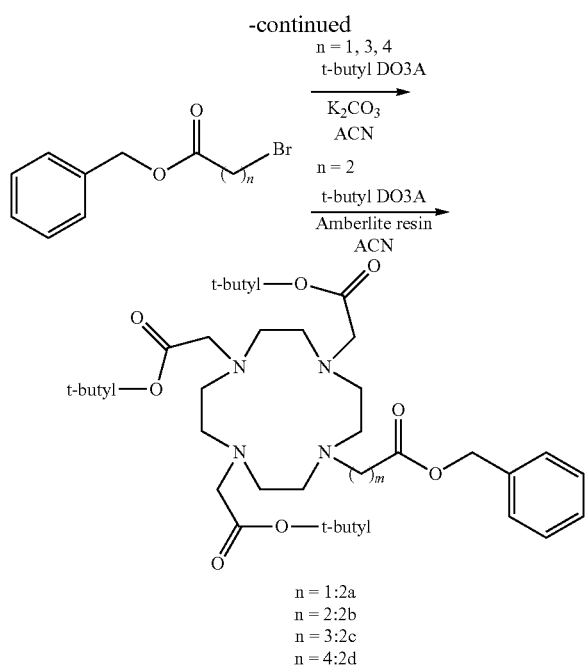

n = 1:2a
n = 2:2b
n = 3:2c
n = 4:2d

The protected 3-carbon (1c) and 4-carbon linker (1d) arms (benzyl 4-bromobutyrate and benzyl 5-bromovalerate respectively) were synthesized by benzyl protecting 4-bromobutyric acid and 5-bromovaleric acid using benzyl alcohol and esterification agents DIC and DPTS (Scheme 1). These protected linkers were conjugated to the tert-butyl protected DO3A macrocycle via an SN2 reaction using K2CO3 and reflux conditions to produce 2a, 2c, and 2d.

Benzyl protection of 3-bromopropionic acid (1b) was achieved in high yield using a previously described method (Scheme 1) (see, e.g., McCabe, P. H.; Milne, N. J.; Sim, G. A. J. Chem. Soc., Perkin Trans. 2 1989, 1459; herein incorporated by reference in its entirety). 3-Bromopropionic acid was heated to reflux with benzyl alcohol in toluene using p-toluene sulfonic acid monohydrate as a catalyst. A new procedure for synthesis of a monopropionate derivative of DOTA is described in Scheme 2b—initial tests with K2CO3 or Na2CO3 did not produce the desired product (2b). A competing side reaction results in the formation of an α,β-unsaturated product via the elimination of the β-bromide (see, e.g., Jaszberenyi, Z.; Chem. Commun. (Camb) 2009, 6475; herein incorporated by reference in its entirety). The propionate linker (1b) was coupled to the tert-butyl DO3A macrocycle using an anion exchange resin (Amberlite IRA-410 resin) at room temperature to produce 2b.

Scheme 2. Synthesis of Macrocyclic Gd(III) Contrast Agents Connected to Haloalkane Moieties by Linkers of Varying Length

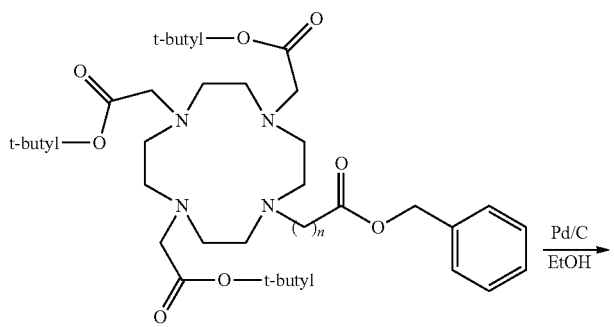

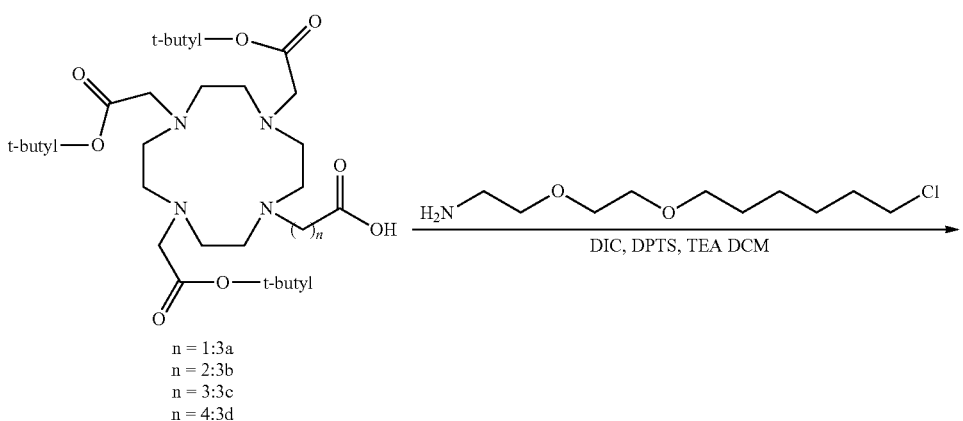

n = 1:3a
n = 2:3b
n = 3:3c
n = 4:3d

-continued

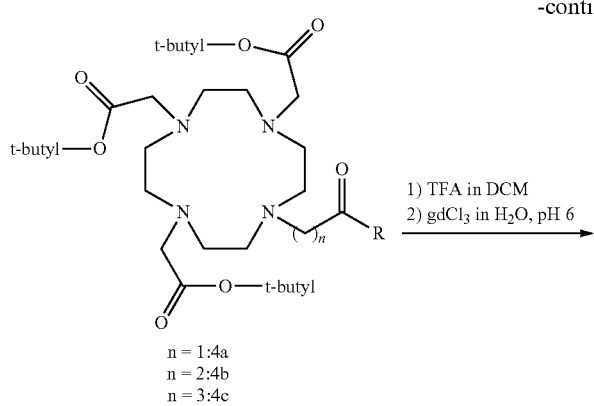

n = 1:4a
n = 2:4b
n = 3:4c
n = 4:4d

1) TFA in DCM
2) gdCl₃ in H₂O, pH 6

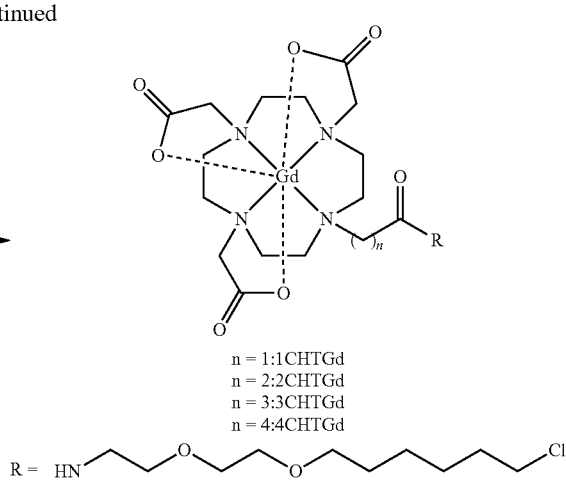

n = 1:1CHTGd
n = 2:2CHTGd
n = 3:3CHTGd
n = 4:4CHTGd

R = HN~~O~~O~~Cl

The final products were prepared using the approach shown in Scheme 2. The benzyl protecting group on the linker arm was removed via hydrogenation using a palladium on carbon catalyst to produce the free carboxylic acid. The haloalkane moiety was peptide coupled to the free acid of the tert-butyl DO3A-linker using DIC, DPTS, and TEA. The tert-butyl protecting groups were removed with trifluoroacetic acid, and the final complexes were produced by metalation with GdCl3 maintaining the pH below 6. The metalated complexes were purified by reverse-phase HPLC and characterized by MS. No aggregation was observed in relaxometric measurements.

The HaloTag protein was expressed recombinantly after subcloning the target protein into the vector pMCSG7 to include an N-terminal His6-Tag followed by a TEV protease cleavage site. The protein was expressed in BL21(DE3) cells and purified by Nickel affinity chromatography. The affinity tag was proteolytically removed with TEV protease, and HaloTag protein was further purified by ion exchange and gel-filtration chromatography (the resulting protein was >99% pure by SDS-PAGE). The HaloTag protein was labeled with a 5-fold molar excess of the Gd(III) complex at 4 degrees C. overnight. The excess was removed via a desalting column followed by dialysis overnight into 10 mM MOPS pH7.4 resulting in a 1:1 Gd(III) complex-protein species. The labeled proteins were concentrated to a starting concentration of ~600 µM for all relaxivity analyses.

Longitudinal relaxivities of the unbound agents were determined in water and the protein-bound contrast agents in 10 mM MOPS at 1.5 T, 37_C (Table 1). The agents that possess shorter linkers (1CHTGd and 2CHTGd) had relaxivities similar to those of reported agents coordinating one water molecule (see, e.g., Caravan, P.; Ellison, J. J.; McMurry, T. J.; Lauffer, R. B. Chem. Rev. 1999, 99, 2293; herein incorporated by reference in its entirety). It is possible that an unfavorable geometry prevents the carbonyls in 3CHTGd and 4CHTGd from coordinating the Gd(III) providing an additional coordination site for water, resulting in their slightly larger observed relaxivities.

TABLE 1

Longitudinal Relaxivities of Free (F) and Protein-Bound (PB) HaloTag Targeted Contrast Agents at 60 MHz, 37° C.

| Sample | $r_1$ - F ($mM^{-1}s^{-1}$) | $r_1$ - PB ($mM^{-1}s^{-1}$) | Fold Change |
|---|---|---|---|
| 1CHTGd | 3.6 ± 0.2 | 13.4 ± 1.3 | 3.7 |
| 2CHTGd | 3.8 ± 0.1 | 22.0 ± 2.2 | 5.8 |
| 3CHTGd | 5.1 ± 0.1 | 7.6 ± 0.7 | 1.5 |
| 4CHTGd | 6.4 ± 0.5 | 8.6 ± 1.1 | 1.3 |

The relaxivities of the protein-bound contrast agents do not follow a trend with linker length and vary significantly, from 7.6 to 22.0 mM⁻1s⁻1 (Table 1). The bound 2CHTGd demonstrated the largest difference in relaxivity with a 6-fold increase from 3.8 to 22.0 mM⁻1s⁻1. This increase in relaxivity is similar to that of MS-325, which increases from 5.5 to 25 mM⁻1s⁻1 (1.5 T, 37 degrees C.) when bound to HSA.4b This result reflects an effective linker length that couples the rotational correlation time of the Gd(III) chelator to the HaloTag protein. Complexes 1-, 3-, and 4CHTGd, showed a lesser increase in relaxivity upon binding to the protein; 3CHTGd and 4CHTGd resulted in the smallest change in r1, while 1CHTGd had an intermediate increase in r1 when protein-bound.

Figure 13:
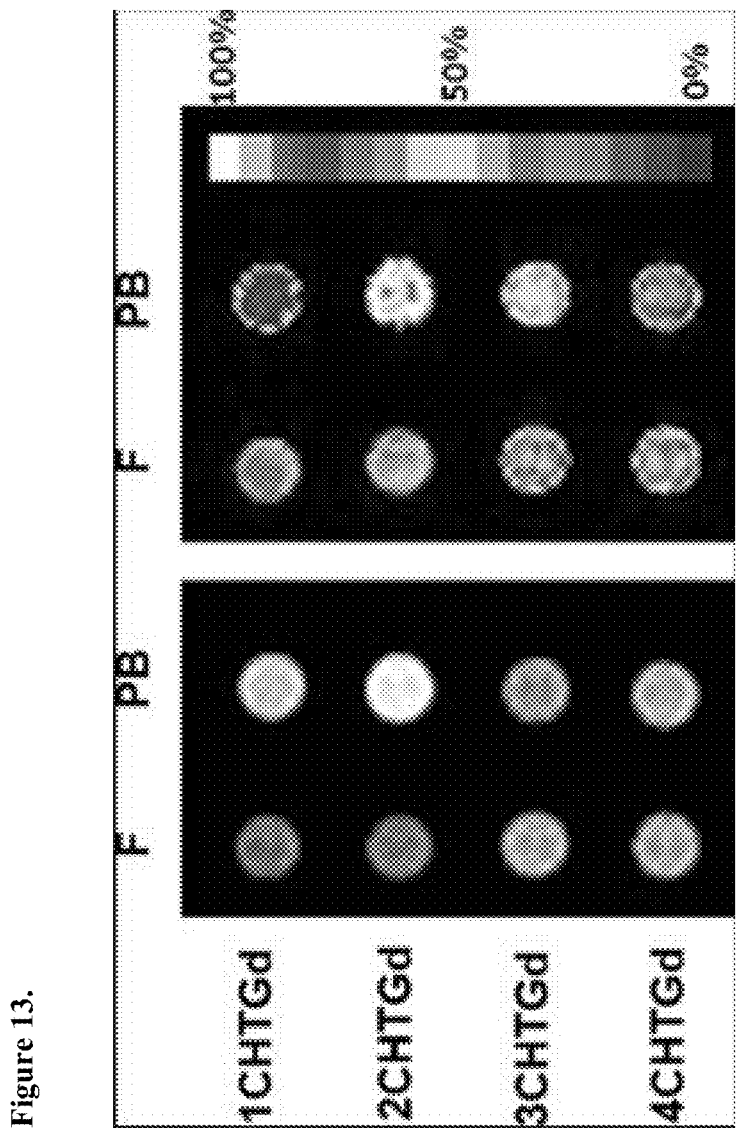
FIG. 13 shows MR images of HaloTag-targeted contrast agents. Gray-scale (left panel) and intensity-scale (right panel) T1-weighted images of the free (F) and protein-bound (PB) contrast agents (100 µM Gd(III)) obtained at 1.5 T (TR 150 ms, TE 3.6 ms).

This range in signal enhancement was visualized by acquiring MR images at 1.5 T (FIG. 13). The phantoms (100 µM solutions of 1CHTGd, 2CHTGd, 3CHTGd, 4CHTGd, 1CHTGd-Pro, 2CHTGd-Pro, 3CHTGd-Pro, 4CHTGd-Pro) confirmed the longitudinal relaxivity results. A difference of a single carbon had a significant effect on the relaxation properties of the proteinbound agent.

The relatively low relaxivities of the bound 1-, 3-, and 4CHTGd complexes, compared to 2CHTGd, can be attributed to one or a combination of unoptimized relaxation parameters, τR, τM, or q. As discussed previously, relaxivity increases achieved from binding a protein can be impacted by the rapid local motion of the Gd(III) chelator. For example MP-2269, a serum albumintargeted contrast agent that is similar to MS-325, achieves only half the protein-bound relaxivity of MS-325 due to its TR being an order of magnitude shorter.14 The short τR of the protein-bound MP-2269 is attributed to the internal flexibility which allows free rotation of the Gd(III) complex.14 In addition, several amino acid residues have the potential to coordinate Gd(III)

(such as the hydroxyl groups in serine and threonine, amines in lysine, and carboxylic acids in glutamic and aspartic acids). It is possible for nearby residues to displace the inner-sphere water of the bound contrast agent causing coordinative saturation and a decrease in observed relaxivity (see, e.g., Aime, S.; J. Biol. Inorg. Chem. 2000, 5, 488; Zech, S. G.; Sun, W. C.; Jacques, V.; Caravan, P.; Astashkin, A. V.; Raitsimring, A. M. Chem Phys Chem 2005, 6, 2570; each herein incorporated by reference in its entirety).

HaloTag Protein Expression and Purification

The HaloTag plasmid was purchased from Promega Biosciences. The gene was subcloned into the pMCSG7 vector adding an N-terminal His6-Tag to ease the purification. Protein expression was induced with IPTG in Terrific Broth in BL21*DE3 E. coli (18 hrs, 16° C.) and purified by Nickel affinity chromatography, Q-sepharose ion exchange chromatography and S-100 size exclusion chromatography. The pure protein was desalted into 10 mM MOPS pH 7.4 using an Econo-Pac 10DG Column (Bio Rad). The yield was optimized to 45 mg/L culture. Protein identity was confirmed by mass spectrometry (Voyager DE Pro MALDI-MS) and 10 pmol HaloTag samples were mixed with sinapic acid matrix (saturated solution) for analysis.

HaloTag Protein Labeling Procedure

To prepare the protein-bound contrast agent 12.5 mg protein was incubated overnight at 4° C. with five equivalents haloalkane label. Excess label was removed by size-exclusion chromatography (Econo-Pac 10 DG Disposable Chromatography Columns) and dialysis overnight into 10 mM MOPS, pH 7.4 (Spectrum Spectra/Por 4 Dialysis Membrane Tubing 12-14K MWCO) at 4° C. The protein-bound contrast agent was concentrated to a starting concentration of ~600 µM for all relaxivity assays (Amicon Ultra-4, PLGC Ultracel-PL Membrane, 10 kDa). Agent binding was detected by mass spectrometry (Agilent 6510 Accurate-Mass Q-TOF LC/MS) and data deconvolution was performed with the included software (Agilent MassHunter Qualitative Analysis). The masses were within 1.0 Da of those predicted. No free contrast agent was detected.

Relaxivity Determination

The relaxation rates and Gd(III) concentrations were determined for contrast agent solutions in a range of concentrations. The relaxation rates of small molecule contrast agents were investigated using a 4 mM starting solution in water and diluted 1:1 four times. Relaxation rates of protein bound contrast agents were measured using 600 µM starting solution in 10 mM MOPS and was diluted 1:1 four times. Relaxation rates were determined using a 60 MHz (1.5 T) NMR analyzer (Bruker Minispec MQ60) at 37° C. using 500 µL in a 7.5 mm inner diameter NMR tubes. T1 relaxation times were determined using monoexponential curve fitting and an inversion recovery pulse sequence with four averages for each of 10 data points.

Gd(III) concentrations for all samples were measured by ICP-MS. Samples were prepared by dissolving 10 µL into 90 µL trace nitric acid, and diluted to 10 mL with ultrapure water (nitric acid was added to generate a 3% solution. Samples contained a multi-element internal standard consisting of 5 ppb each Bi, Ho, In, Li(6), Sc, Tb, and Y (Spex Certiprep, Metuchen, N.J., USA). ICP-MS was performed on a computer-controlled (Plasmalab software) Thermo X series II ICP-MS (Thermo Fisher Scientific, Waltham, Mass., USA) equipped with an ESI SC-2 autosampler (Omaha, Nebr., USA). Each sample was acquired using 1 survey run (10 sweeps) and 3 main (peak jumping) runs (100 sweeps).

Figure 14:
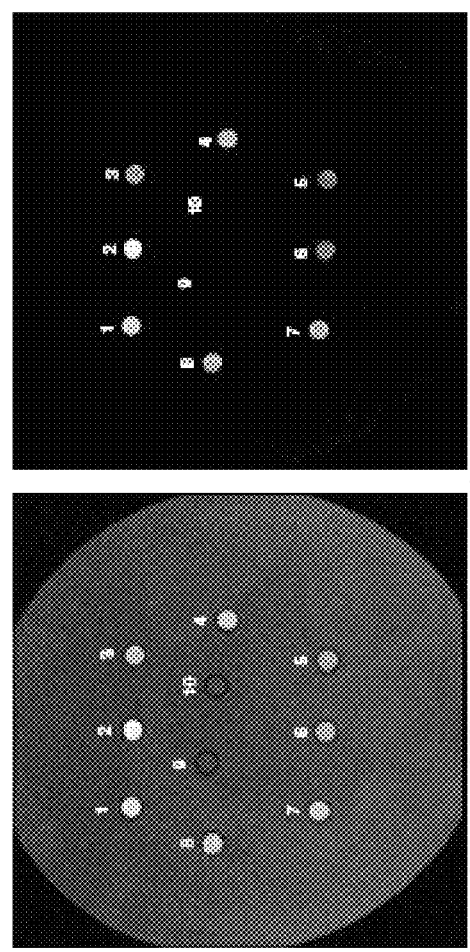
FIG. 14 shows unedited (left) and brightness-adjusted (right) 1.5 T MR image of the unbound and bound HaloTag targeted complexes and controls. The two control samples (9 and 10) show no difference to the water in which they were submerged
1) 1CHTGd-Pro (100 µM)
2) 2CHTGd-Pro (100 µM)
3) 3CHTGd-Pro (100 µM)
4) 4CHTGd-Pro (100 µM)
5) 1CHTGd (100 µM)
6) 2CHTGd (100 µM)
7) 3CHTGd (100 µM)
8) 4CHTGd (100 µM)
9) Unlabelled HaloTag Protein (100 µM)
10) 10 mM MOPS buffer, pH 7.4.

Magnetic Resonance Imaging 1 mL solutions of 100 µM 1CHTGd, 2CHTGd, 3CHTGd, 4CHTGd and HaloTag bound complexes in 10 mM MOPS, pH 7.4 were prepared and their concentration verified by ICP-MS analysis. Samples were submerged in water and imaging was performed on a Siemens 1.5 T Espree using the following parameters: TR 150 ms, TE 3.6 ms, 50 degree flip angle. Controls of buffer and 100 µM unlabeled HaloTag solutions were included. These solutions were indistinguishable from the background (FIG. 14).

Synthesis—General Notes

All compounds were purchased from Sigma Aldrich (St. Louis, Mo.) and used without further purification. 1H and 13C NMR spectra were obtained on a Bruker 500 MHz Avance III NMR Spectrometer with CDCl3. Electrospray ionization mass spectrometry (ESI-MS) spectra were obtained on a Varian 1200 L single-quadrupole mass spectrometer. Analytical reversephase HPLC-MS was performed on a Varian Prostar 500 system with a Waters 4.6×250 mm 5 µM Atlantis C18 column. This system is equipped with a Varian 380 LC ELSD system, a Varian 363 fluorescence detector, and a Varian 335 UV/Vis detector. Preparative runs were performed on a Water 19×250 mm Atlantis C18 Column. The mobile phases consisted of Millipore water (A) and HPLC-grade acetonitrile (B).

Synthesis of Haloalkane Moiety

CBZ-Protected Amino Ethoxy Ethanol (S1)

1-amino-2-ethoxyethanol (1.358 mL, 9.5 mmol) was dissolved in 20 mL 10% triethylamine in MeOH and cooled to 0° C. Benzyl chloroformate (0.946 mL, 9.5 mmol) was added all at once, and the reaction was allowed to warm to room temperature overnight. The solvent was removed by evaporation, and the product purified using silica column chromatography, resulting in a colorless oil (95% yield).

1H NMR (500 MHz, CDCl3) 2.69 (bs, 1H), 3.36 (t, 2H), 3.50 (m, 4H), 3.67 (t, 2H), 5.07 (s, 2H), 5.78 (bs, 1H), 7.32 (m, 5H)

13C NMR (125 MHz, CDCl3) 40.83, 61.48, 66.71, 70.07, 72.27, 128.13, 128.51, 136.52, 156.81

CBZ Protected Haloalkane (S2)

CBZ-protected amino-ethoxyethanol (1.505 g, 6.3 mmol) was stirred vigorously with 40% KOH in water (4.67 mL, 31.5 mmol) and 100 µL tertbutylyammonium hydroxide 40% in water for 1 hour. 1-bromo-6-chlorohexane (4.41 mL, 31.5 mmol) was added all at once and the reaction was allowed to proceed overnight. The product was extracted into ethyl acetate, washed with water and brine, and purified by silica column chromatography (40% ethyl acetate in hexanes). (60% yield)

M/Z calculated: 357.17, observed: 380.0 [M+Na]+

1H NMR (500 MHz, CDCl3) 1.34 (p, 2H), 1.41 (p, 2H), 1.58 (p, 2H), 1.74 (p 2H), 3.39 (q, 2H), 3.44 (t, 2H), 3.49 (t, 2H), 3.55 (m, 4H), 3.59 (m, 2H), 5.09 (s, 2H), 5.43 (bs, 1H), 7.34 (m, 5H) 13C NMR (125 MHz, CDCl3) 25.25, 26.61, 29.36, 40.79, 45.02, 66.56, 69.96, 70.22, 71.22, 128.02, 128.03, 128.44, 136.58, 156.45

Amine Terminated Haloalkane (S3)

Compound 6 (1.513 g, 4.24 mmol) dissolved in 100 mL EtOH was added to a hydrogenator flask containing 500 mg Pd/C. The reaction mixture was agitated under H2 at 40 psi for 12-24 hours. The Pd/C was removed by filtration and the EtOH removed by evaporation. (93% yield)

1H NMR (500 MHz, CDCl3) 1.37 (p, 2H), 1.46 (p, 2H), 1.60 (p, 2H), 1.78 (p, 2H), 2.99 (t, 2H), 3.47 (t, 2H), 3.54 (t, 2H), 3.58 (m, 2H), 3.63 (m, 4H), 5.10 (s, 2H) 13C NMR (125 MHz, CDCl3) 25.31, 26.60, 29.33, 32.45, 40.56, 45.02, 69.90, 70.20, 70.48, 71.17

General Procedure for Benzyl Protection of the Bromo-Acid (1c, 1d)

Diisopropylcarbodiimide (DIC) (3.59 mmol, 1.3 eq) was added to a mixture of the bromo-acid (4-bromobutyric acid or 5-bromovaleric acid) (2.76 mmol, 1 eq) and DPTS (3.04 mmol, 1.1 eq) in dry DCM (30 mL) and was allowed to react for 2 hours at room temperature. Benzyl alcohol (4.14 mmol, 1.5 eq) was added and allowed to react overnight. The reaction was washed water and brine, and the DCM was removed by evaporation. Hexanes was added and the resulting white precipitate was removed by filtration. The hexanes was removed from the filtrate by evaporation resulting in an oil which was purified by silica gel chromatography (Hexanes/Ethyl Acetate 3.5/1).

Benzyl 4-bromobutyrate (1c)

70% yield
1H NMR (500 MHz, CDCl3) 2.22 (p 2H), 2.58 (t, 2H), 3.48 (t, 2H), 5.16 (s, 2H), 7.40 (m, 5H)
13C NMR (125 MHz, CDCl3): 28.0, 32.7, 33.0, 66.7, 128.5, 128.6, 128.9, 136.1, 172.6

Benzyl 5-bromovalerate (1d)

95% yield
1H NMR (500 MHz, CDCl3) 1.79 (m, 2H), 1.88 (m, 2H), 2.38 (t, 2H), 3.38 (t, 2H), 5.11 (s, 2H),
7.35 (m, 5H)
13C NMR (125 MHz, CDCl3) 23.44, 31.91, 33.03, 33.22, 66.25, 128.21, 128.24, 128.56, 135.88,
172.89

Synthesis of Benzyl 3-Bromopropionate (1b)

Benzyl-3-bromopropionate 3-bromopropionic acid (15 g, 98 mmol) and benzyl alcohol (9.42 mL, 91 mmol) were dissolved in 100 mL dry toluene. A catalytic amount of toluene sulfonic acid monohydrate (1.86 mg, 0.98 mmol) was added. A dean stark apparatus and condenser was applied and the mixture was heated to 140° C. overnight, the toluene/water azeotrope mixture was removed three times. The toluene was removed by evaporation and the mixture was redissolved in ethyl acetate. The solution was washed with saturated NaHCO3 solution and the ethyl acetate removed by evaporation.

1H NMR (500 MHz, CDCl3) 2.92 (t, 2H), 3.09 (t, 2H), 5.18 (s, 2H), 7.36 (m, 5H)
13C NMR (125 MHz, CDCl3) 25.02, 37.65, 66.73, 128.29, 128.37, 128.57, 135.46, 170.30

General Method for Linker Addition to t-Butyl-DO3A (2a, 2c, 2d)

Under N2, t-butyl-DO3A (0.939 g, 1.827 mmol, 1 eq), the benzyl protected bromo-acid (4a or 4c or 4d) (2.740 mmol, 1.5 eq), and K2CO3 (0.756 g, 5.48 mmol, 3 eq) were added to 50 mL dry ACN. This was allowed to reflux at 75° C. overnight. The K2CO3 was filtered away and the ACN removed by evaporation. The reaction was diluted with DCM and washed three times with water, and three times with brine. The product was purified by silica gel chromatography with a gradient from 7% to 12% MeOH in DCM.

t-butyl-DO3A-benzyl acetate (2a)

(95% yield) M/Z calculated: 662.43, observed: 663.99 [M+H]+

1H NMR (500 MHz, CDCl3) 1.46 (m, 27H), 2-4 (broad peaks, 24H), 5.07 (s, 2H), 7.32 (m, 5H)
13C NMR (125 MHz, CDCl3) 28.02, 48.67, 50.04, 52.74, 55.49, 55.96, 56.61, 81.87, 81.99,
82.23, 126.50, 126.67, 126.75, 134.01, 169.87, 172.79, 174.79 t-butyl-DO3A-benzyl butyrate (2c)

(98% yield) M/Z calculated: 690.457, observed: 691.455 [M+H]+
1H NMR (500 MHz, CDCl3) 1.44 (m, 27H), 1.77 (t, 2H), 2-4 (broad peaks, 26H), 5.09 (s, 2H), 7.34 (m, 5H)
13C NMR (125 MHz, CDCl3) 25.79, 29.92, 47.89, 54.34, 54.66, 64.10, 79.55, 80.33, 80.67,
126.00, 126.18, 126.45, 133.64, 167.86, 170.56 t-butyl-DO3A-benzyl valerate (2d)

(81% yield) M/Z calculated: 704.47, observed: 705.39 [M+H]+
1H NMR (500 MHz, CDCl3) 0.88 (broad peak, 27H), 1-3 ppm (broad peaks, 30H), 4.52 (s, 2H),
6.77 (s, 5H)
13C NMR (125 MHz, CDCl3) 22.50, 25.56, 27.56, 27.69, 27.87, 33.67, 47.25, broad peaks 47.25-56.62, 65.70, 80.96, 82.31, 127.87, 127.91, 128.0, 135.77, 169.74, 172.53 t-Butyl-DO3A-Benzyl Propionate (2b)

Synthetic Note: several approaches to generate the monopropionate derivative of DOTA have been described in previous literature, including direct modification of t-butyl DO3A modification of cyclen glyoxal, and modification of cyclen with a propionate arm. These approaches result in low yields and require additional synthetic steps. Direct modification of tbutyl DO3A using anion-exchange resin was used to prepare a monopropionate derivative of DOTA and can be accomplished at room temperature with few side-products.

Amberlite IRA-410 resin (2 g) was washed with water, activated with 60 mL 1M NaOH, washed with water until neutral, and washed with ACN. The resin was suspended in 30 mL dry ACN and t-butyl-DO3A (500 mg, 0.972 mmol) added. Benzyl 3-bromopropionate (700 mg, 2.918 mmol) was added dropwise, and the reaction allowed to proceed overnight. The resin was filtered away, the ACN removed by evaporation, the reaction mixture dissolved in DCM and washed with saturated K2NO3. The product was purified using silica column chromatography. (84% yield)

M/Z calculated: 676.4, observed: 677.1 [M+H]+
1H NMR (500 MHz, CDCl3) 1.45 (s, 27H), 2-3.5 ppm (broad peaks, 26H), 5.10 (s, 2H), 7.34 (m,
5H)
13C NMR (125 MHz, CDCl3) 27.82, 27.89, 28.16, 30.91, 49.88, 55.68, 55.44, 66.37, 82.26,
82.46, 128.04, 128.35, 128.58, 135.46, 172.43, 172.74, 173.08

General Method for Deprotection of Benzyl Group (3a-3d)

5a-5d was dissolved in 50 mL EtOH was added to a hydrogenator flask containing 500 mg Pd/C. The reaction mixture was agitated under H2 at 40 psi for 12-24 hours. The Pd/C was removed by filtration and the EtOH removed by evaporation. Compounds were analyzed by TLC for the presence of carboxylic acid and used without further purification.

General Method for Peptide Coupling the t-Butyl-DO3A-Reactive Linker (4a-4d)

6a, DIC, DPTS and TEA were added to dry DCM and allowed to react for two hours. Compound 3 was added all at once, and the reaction was allowed to proceed overnight. The reaction was washed with water and brine, and the DCM was removed by evaporation. The resulting oil was purified by silica chromatography using a 6%-12% gradient of MeOH in DCM. Compounds were analyzed by mass spectrometry only. NMR could not be used for analysis due to peak broadening resulting from the macrocycle.

4a—M/Z calculated: 777.502. observed: 778.6 [M+H]+ (86% yield).

4b—M/Z calculated: 791.52. observed: 792.96 [M+H]+ (58% yield).

4c—M/Z calculated: 805.53. observed: 806.36 [M+H]+ (71% yield).

4d—M/Z calculated: 819.549. observed: 820.6 [M+H]+ (36% yield).

General Method for Synthesis of Final Compounds (1-, 2-, 3-, 4CHTGd)

The t-butyl protecting groups were removed by dissolving 7a in 2 mL DCM and 2 mL trifluoroacetic acid. The reaction was allowed to proceed for 2 days, and the acid was removed by evaporation. After all the acid was removed, the mixture was dissolved in 2 mL water and 1.2 equivalents GdCl3.6H2O was added slowly, maintaining the pH below 6. The final compound was purified by reverse phase HPLC and analyzed for purity by analytical HPLC.

1CHTGd—M/Z calculated: 764.215. observed: 764.0 [M+H]+.

2CHTGd—M/Z calculated: 778.23. observed: 778.2 [M+H]+.

3CTHGd—M/Z calculated: 792.246. observed: 795.6 [M+H]+.

4CHTGd—M/Z calculated: 806.262. observed: 807.230 [M+H]+.

SUPPLEMENTAL TABLE 1

Transverse relaxivities of free (F) and protein-bound (PB) HaloTag targeted contrast agents at 60 MHz, 37° C.

| Sample | $r_2$ - F ($mM^{-1}s^{-1}$) | $r_2$ - PB ($mM^{-1}s^{-1}$) |
|---|---|---|
| 1CHTGd | 4.1 ± 0.2 | 25.2 ± 2.6 |
| 2CHTGd | 3.9 ± 0.5 | 45.3 ± 5.5 |
| 3CHTGd | 5.8 ± 0.1 | 13.1 ± 0.9 |
| 4CHTGd | 6.5 ± 0.5 | 15.9 ± 2.3 |

SUPPLEMENTAL TABLE 2

Transverse and longitudinal relaxivities of free (F) and protein-bound (PB) HaloTag targeted contrast agets at 400 MHz, 37° C.

| Sample | $r_1$ - F ($mM^{-1}s^{-1}$) | $r_2$ - F ($mM^{-1}s^{-1}$) | $r_1$ - PB ($mM^{-1}s^{-1}$) | $r_2$ - PB ($mM^{-1}s^{-1}$) |
|---|---|---|---|---|
| 1CHTGd | 3.2 ± 0.1 | 4.0 ± 0.1 | 4.0 ± 0.2 | 28 ± 2 |
| 2CHTGd | 3.3 ± 0.1 | 4.1 ± 0.1 | 5.1 ± 0.7 | 56 ± 8 |
| 3CHTGd | 6.0 ± 0.2 | 4.9 ± 0.2 | 2.7 ± 0.1 | 15.9 ± 0.1 |
| 4CHTGd | 5.6 ± 0.2 | 6.9 ± 0.2 | 3.3 ± 0.2 | 19.6 ± 1.3 |

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

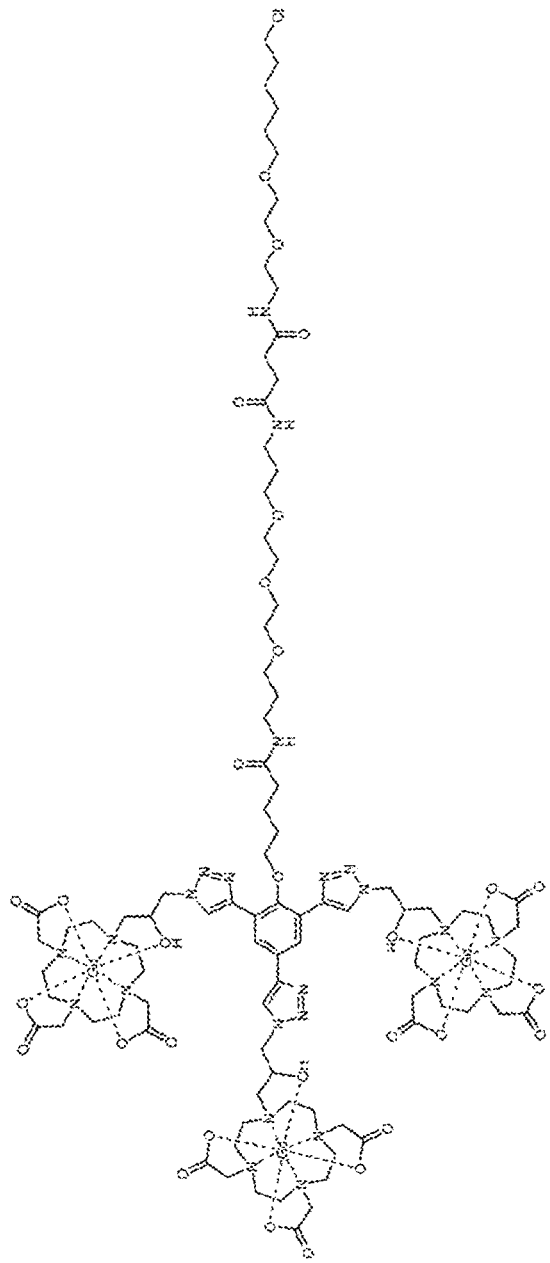

We claim:

1. A composition comprising an MRI contrast agent, wherein the MRI contrast agent is Supplemental Scheme 1. Synthesis of a 14-atom haloalkane moiety for targeting and binding the HaloTag reporter protein.

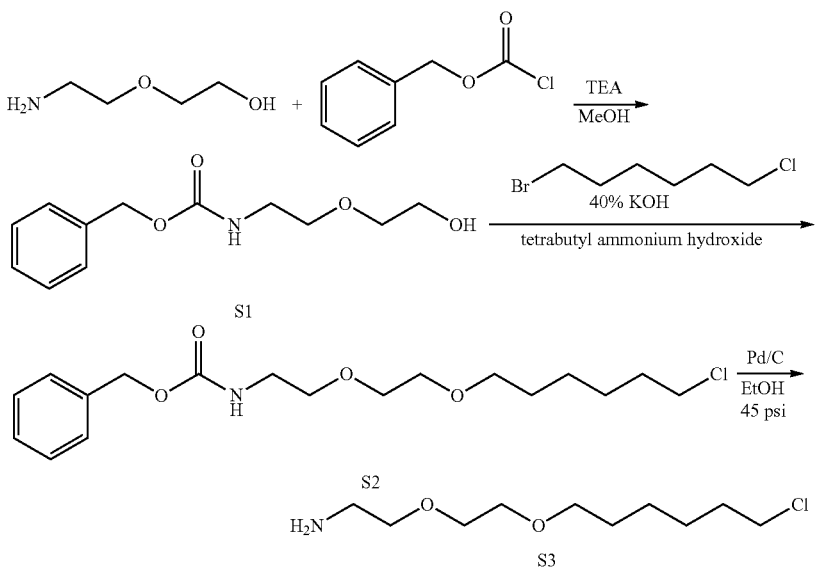

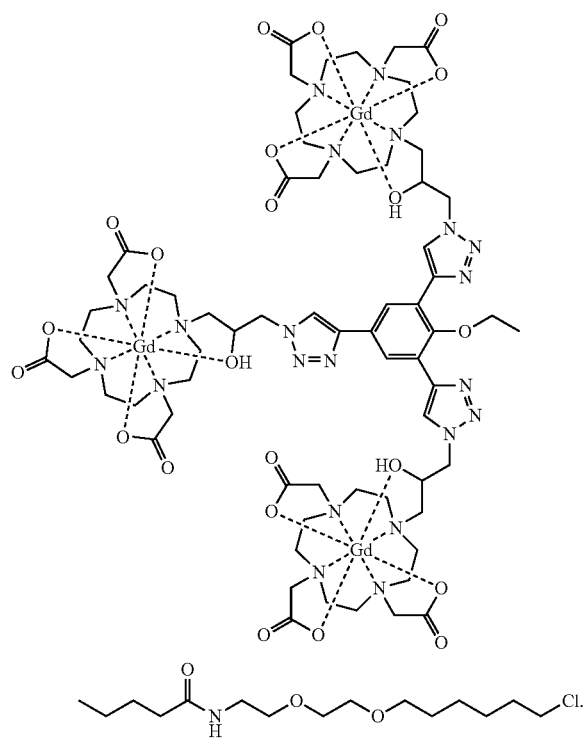

2. The composition of claim 1, wherein said MRI contrast agent is configured to attach with a HaloTag protein.

3. The composition of claim 1, wherein said MRI contrast agent has tunable relaxation properties thereby providing optimal relaxivity for low field strength imaging and the other optimal relaxivity for high field strength MR imaging.

4. A method of imaging, comprising expressing a HaloTag/gene of interest construct in a cell, administering a MRI contrast agent configured to attach with said Halo Tag/gene of interest, and imaging said attached MRI contrast agent with said Halo Tag/gene of interest, wherein said MRI contrast agent is

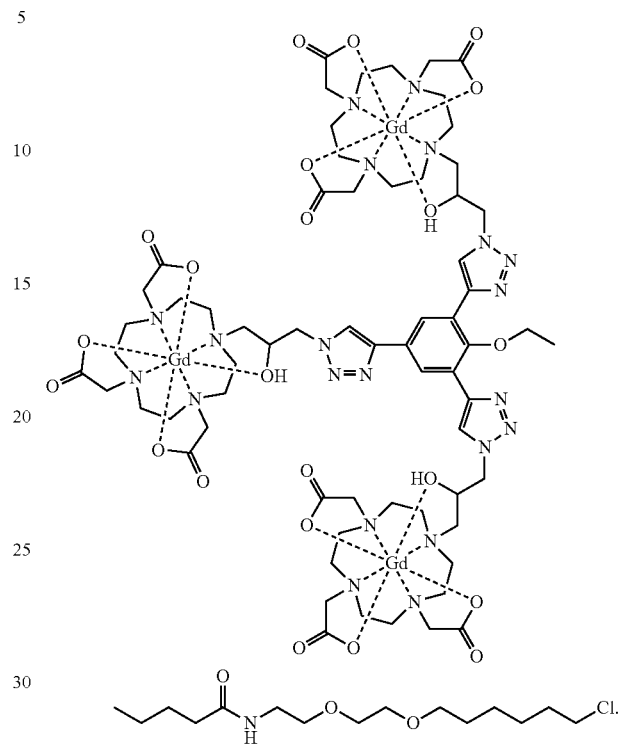

5. The method of claim 4, wherein said imaging relates to detecting gene expression (of a gene of interest) in real time in vivo, detecting changes in gene expression (of a gene of interest) over time in an individual organism, detecting gene expression changes (of a gene of interest) in response to therapeutics, and detecting cell labeling for MR imaging.

* * * * *

UNITED STATES PATENT AND TRADEMARK OFFICE
CERTIFICATE OF CORRECTION

PATENT NO.        : 9,585,975 B2
APPLICATION NO.   : 13/853324
DATED             : March 7, 2017
INVENTOR(S)       : Thomas J. Meade, Renee C. Strauch and Luke F. Vistain Page 1 of 2

It is certified that error appears in the above-identified patent and that said Letters Patent is hereby corrected as shown below:

In Claim 1, Column 23, the compound in Line 1 should read:

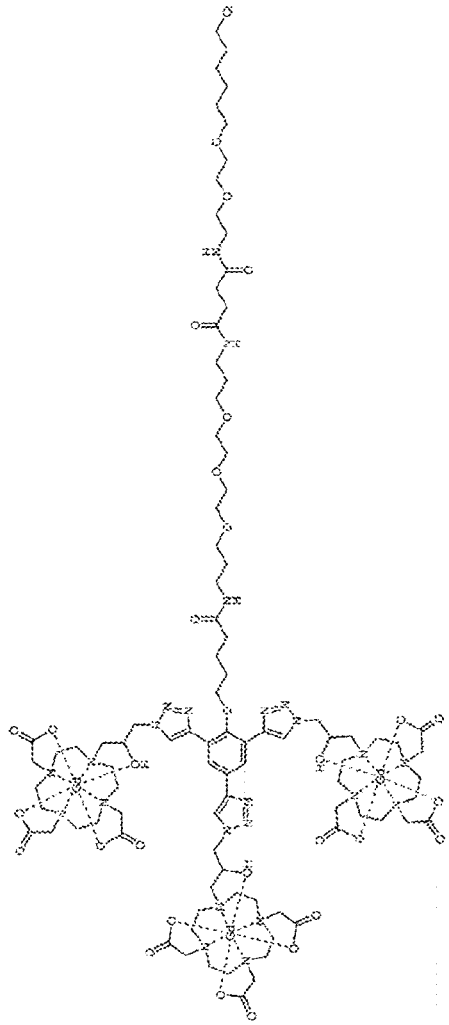

Signed and Sealed this
Twenty-second Day of May, 2018

Andrei Iancu
*Director of the United States Patent and Trademark Office*

CERTIFICATE OF CORRECTION (continued)
U.S. Pat. No. 9,585,975 B2

In Claim 4, Column 24, the compound starting on Line 5 should read: